United States Patent
DiMarco et al.

(10) Patent No.: US 6,689,802 B2
(45) Date of Patent: Feb. 10, 2004

(54) POLYMORPHS OF AN EPOTHILONE ANALOG

(75) Inventors: John D. DiMarco, East Brunswick, NJ (US); Jack Z. Gougoutas, Princeton, NJ (US); Imre M. Vitez, Whitehouse Station, NJ (US); Martha Davidovich, East Brunswick, NJ (US); Michael A. Galella, Old Bridge, NJ (US); Timothy M. Malloy, Yardley, PA (US); Zhenrong Guo, East Brunswick, NJ (US); Denis Favreau, Saint-Hubert (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/925,112

(22) Filed: Aug. 9, 2001

(65) Prior Publication Data

US 2002/0188014 A1 Dec. 12, 2002

Related U.S. Application Data

(60) Provisional application No. 60/225,590, filed on Aug. 16, 2000.

(51) Int. Cl.[7] .................. C07D 493/04; A61K 31/42
(52) U.S. Cl. .................. 514/365; 540/456; 540/462
(58) Field of Search ................ 514/365; 540/462, 540/456

(56) References Cited

U.S. PATENT DOCUMENTS

| 6,194,181 B1 | 2/2001 | Hofmann et al. ............ 435/18 |
| 6,204,388 B1 | 3/2001 | Danishefsky et al. ....... 546/340 |

FOREIGN PATENT DOCUMENTS

| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/03848 | 1/1999 |
| WO | 99/07692 | 2/1999 |
| WO | 99/39694 | 8/1999 |
| WO | 99/42602 | 8/1999 |
| WO | 99/43320 | 9/1999 |
| WO | 99/43653 | 9/1999 |
| WO | 99/27890 | 10/1999 |
| WO | 00/00485 | 1/2000 |
| WO | 00/37473 | 6/2000 |
| WO | 00/66589 | 11/2000 |

OTHER PUBLICATIONS

Balog, A., et al., "Total Synthesis of (-)-Epothilone A", *Angew. Chem. Int. Ed. Engl.*, Vol. 35, No. 23/24, 2801–2803 (1996).

Bertini, F., et al., "Alkenes from Epoxides by Reductive Elimination with Magnesium Bromide–Magnesium Amalgam", *Chem. Commun.*, 144 (1970).

Bollag, D.M., et al., "Epothilones, A New Class of Microtubule–stabilizing Agents with a Taxol–like Mechanism of Action", *Cancer Res.* 55, No. 11, 2325–2333 (1995).

Fujisawa, T., et al., "Deoxygenation of Epoxides to Olefins with $FeCl_3$—n—BuLi System", *Chem. Lett.*, 883–886 (1974).

Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.*, Vol. 43, No. 12, 2477–2479 (1978).

Gladysz, J. A., et al., "Deoxygenation of Epoxides by Metal Atom Cocondensation", *J. Org. Chem.*, Vol. 41, No. 22, 3647–3648 (1976).

Hofle, G., et al., "Epothilone A and B—Novel 16–Membered Macrolides with Cytotoxic Activity: Isolation, Crystal Structure, and Conformation in Solution", *Agnew. Chem. Int. Ed. Engl.*, Vol. 35, No. 13/14, 1567–1569 (1996).

(List continued on next page.)

Primary Examiner—Bruck Kifle
(74) Attorney, Agent, or Firm—Rena Patel

(57) ABSTRACT

There are provided in accordance with the present invention two crystalline polymorphs, designated Form A and Form B, respectively, as well as mixtures thereof, of an epothilone analog represented by the formula

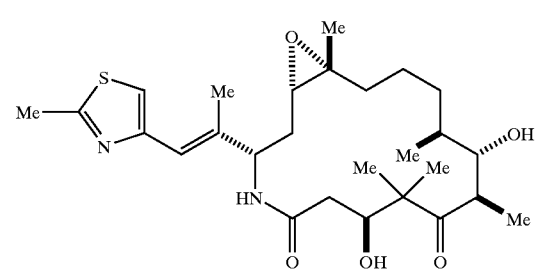

Also provided are methods of forming the novel polymorphs, therapeutic methods utilizing them and pharmaceutical dosage forms containing them.

31 Claims, 9 Drawing Sheets

OTHER PUBLICATIONS

Hofle, G., et al., "N–Oxidation of Epothilone A–C and O–Acyl Rearrangement to C–19 and C–21 –Substituted Epothilones", *Angew. Chem. Int. Ed.,* Vol. 38, No. 13/14, 1971–1974 (1999).

Inokuchi, T., et al., "Opening of Epoxides to Olefins or Halohydrins with Vanadium(II)–Tetrahydrofuran or Vanadium(III)–Tetrahydrofuran Complexes", *Synlett,* No. 6, 510–512 (1992).

Kowalski, R. J., et al., "Activities of the Microtubule–stabilizing Agents Epothilones A and B with Purified Tubulin and in Cells Resistant to Paclitaxel (Taxol®)" *J. Biol. Chem.,* Vol. 272, No. 4, 2534–2541 (1997).

Kupchan, S. M., et al., "Reductive Elimination of Epoxides to Olefins with Zinc–Copper Couple", *J. Org. Chem.,* Vol. 36, No. 9, 1187–1190 (1971).

Martin, M. G., et al., "Epoxides as Alkene Protecting Groups. A Mild and Efficient Deoxygenation", *Tetrahedron Letters,* Vol. 25, No. 3, 251–254 (1984).

McMurry, J. E., et al., "Reduction of Epoxides to Olefins with Low Valent Titanium", *J. Org. Chem.,* Vol. 40, No. 17, 2555–2556 (1975).

McMurry, J. E., et al., "Some Deoxygenation Reactions with Low–Valent Titanium ($TiCl_3$/$LiAlH_4$)", *J. Org. Chem.,* Vol. 43, No. 17, 3249–3254 (1978).

Meng, D., et al., "Remote Effects in Macrolide Formation Through Ring–Forming Olefin Metathesis: An Application to the Synthesis of Fully Active Epothilone Congeners", *J. Am. Chem. Soc.,* Vol. 119, No. 11, 2733–2734 (1997).

Nicolaou, K. C., et al., "An Approach to Epothilones Based on Olefin Metathesis", *Angew. Chem. Int. Ed. Engl.,* Vol. 35, No. 20, 2399–2401 (1996).

Nicolaou, K. C., et al., "Total Synthesis of Epothilone A: The Macrolactonization Approach", *Angew. Chem. Int. Ed. Engl.,* Vol.36, No. 5, 525–527 (1997).

Nicolaou, K. C., et al., "Designed Epothilones: Combinatorial Synthesis, Tubulin Assembly Properties, and Cytotoxic Action against Taxol–Resistant Tumor Cells", *Angew. Chem. Int. Ed. Engl.,* Vol. 36, No. 19, 2097–2103 (1997).

Nicolaou, K. C., et al., "The Olefin Metathesis Approach to Epothilone A and Its Analogues", *J. Am. Chem. Soc.,* Vol. 119, No. 34, 7960–7973 (1997).

Nicolaou, K. C., et al., "Total Syntheses of Epothilones A and B via a Macrolactonization–Based Strategy", *J. Am. Chem. Soc.,* Vol. 119, No. 34, 7974–7991 (1997).

Nicolaou, K. C., et al., "Synthesis of Epothilones A and B in Solid and Solution Phase", *Nature,* Vol. 387, 268–272 (1997).

Nicolaou, K. C., et al., "Synthesis of Epothilones A and B in Soild and Solution Phase" (Correction to *Nature* 387, 268–272 (1997)), *Nature,* 390, 100 (1997).

Raucher, S., et al., "Total Synthesis of (+)–Dihydrocostunolide via Tandem Cope–Claisen Rearrangement", *J. Org. Chem.,* Vol. 51, No. 26, 5503–5505 (1986).

Sato, M, et al., "Reduction of Organic Compounds with Low–Valent Niobium ($NbCl_5$/$NaAlH_4$)", *Chem. Letters,* 157–160 (1982).

Schinzer, D., et al., "Total Synthesis of (–)–Epothilone A", *Angew. Chem. Int. Ed. Engl.,* Vol. 36, No. 5, 523–524 (1997).

Schobert, R., et al., "Reduction and Isomerization of Oxiranes and •–Diazoketones by Various Early Transition Metallocenes", *Synlett,* Vol. 8, 465–466 (1990).

Sharpless, K. B., et al., "Lower Valent Tungsten Halides. A New Class of Reagents for Deoxygenation of Organic Molecules", *J. Amer. Chem. Soc.,* Vol. 94, No.18, 6538–6540 (1972).

Su, D.–S., et al., "Total Synthesis of (–)–Epothilone B: An Extension of the Suzuki Coupling Method and Insights into Structure–Activity Relationships of the Epothilones", *Angew. Chem. Int. Ed. Engl.,* Vol. 36, No. 7, 757–759 (1997).

Su, D.–S., et al., "Structure–Activity Relationships of the Epothilones and the First in vivo Comparison with Paclitaxel", *Angew. Chem. Int. Ed. Engl.,* Vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.,* Vol. 6, No. 7, 893–898 (1996).

Winkler, J. D., et al., "A Model for the Taxol (Paclitaxel)/ Epothilone Pharmacophore", *Bioorg. Med. Chem. Letts.,* Vol. 6, No. 24, 2963–2966 (1996).

Yang, Z., et al., "Total Synthesis of Epothilone A: The Olefin Metathesis Approach", *Angew. Chem. Int. Ed. Engl.,* Vol. 36, No. 1/2, 166–168 (1997).

Bollag, D., et al., "Epothilone, A New Structural Class of Microtubule Stabilizer", Abstract, *Proc. Am. Assoc. Cancer Res.,* Vol. 36, 86 Meet. 454 (1995).

Bollag, D., "Epothilones: Novel Microtubule–Stabilising Agents", *Expert Opin. Invest. Drugs,* Vol. 6, No. 7, 867–873 (1997).

Bertinato, P., et al., "Studies Toward a Synthesis of Epothilone A: Stereocontrolled Assembly of the Acyl Region and Models for Macrocyclization", J. Org. Chem., Vol. 61, No. 23, 8000–8001 (1996).

*Chemical & Engineering News,* "Epothilone Epiphany: Total Syntheses", Vol. 74, No. 52, 24–26 (1996).

*Chemical & Engineering News,* "First Total Synthesis of Epothilone B", Vol. 75, No. 13, 23 (1997).

*Chemical & Engineering News,* "Solid–Phase Epothilone Synthesis Used to Create Analog Library", Vol. 75, No. 20, 33 (1997).

Claus, E., et al., "Synthesis of the C1–C9 Segment of Epothilons", *Tetrahedron Lett.,* Vol. 38, No. 8, 1359–1362 (1997).

De Brabander, J., et al., "Towards a Synthesis of Epothilone A: Rapid Assembly of the C1–C6 and C7–C12 Fragments", *Synlett,* Vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.,* Vol. 38, No. 8, 1363–1366 (1997).

Gerth, K., et al., "Epothilons A and B: Antifungal and Cytotoxic Compounds from *Sorangiusm cellulosum* (Myxobacteria) Production, Physico–chemical and Biological Properties", *J. Antibiotics,* Vol. 49, No. 6, 560–563 (1996).

Marshall, A., "Total Synthesis of Epothilone", *Nature Biotechnology,* Vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.,* Vol. 61, No. 23, 7998–7999 (1996).

Meng, D., et al., "Total Syntheses of Epothilones A and B", *J. Am. Chem. Soc.,* Vol. 119, No. 42, 10073–10092 (1997).

Mensching, S. and Kalesse, M., "Generation of Thiazoles by Column Dehydrogenation of Thiazolidines with $MnO_2$", *J. Prakt. Chem.,* Vol. 339, No. 1, 96–97 (1997).

Mulzer, J. and Mantoulidis, A., "Synthesis of the C(1)–C(9) Segment of the Cytotoxic Macrolides Epothilon A and B", *Tetrahedron Lett.,* Vol. 37, No. 51, 9179–9182 (1996).

Nicolaou, K., et al., "Chemistry Biology and Medicine of Selected Tubulin Polymerizing Agents,"*Pure Appl. Chem.,* Vol. 71, No. 6, 989–997 (1999).

Nicolaou, K., et al., "Total Synthesis of Epothilone E and Related Side–chain Modified Analogues via a Stille Coupling Based Strategy", *Bioorg. Med. Chem.,* Vol. 7, No. 5, 665–697 (1999).

Schinzer, D., et al., "Studies Towards the Total Synthesis of Epothilones: Asymmetric Synthesis of the Key Fragments", *Chem. Eur. J.,* Vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.,* Vol. 38, No. 12, 2061–2064 (1997).

Schinzer, D., et al., "Syntheses of (–)–Epothilone A", *Chem. Eur. J.,* Vol. 5, No. 9, 2483–2491 (1999).

Schinzer, D., et al., "Syntheses of (–)–Epothilone B", *Chem. Eur. J.,* Vol. 5, No. 9, 2492–2500 (1999).

Nicolaou, K. C., et al., "Synthesis and Biological Properties of C12,13–Cyclopropylepothilone A and Related Epothilones", *Chemistry & Biology,* Vol. 5, No. 7, 365–372 (1998).

Altmann, K.H., et al., "Epothilones and Related Structures—A New Class of Microtubule Inhibitors with Patent in vivo Antitumor Activity," Biochim. Biophys Acta, 1470 (2000).

FORM A rotamers about single bonds
C15–C22 and C24–C25 also confirmational change about
C9–C10

FORM B
rotamers about single bonds
C15–C22 and C24–C25
also
confirmational change about
C9–C10

POLYMORPHS OF AN EPOTHILONE ANALOG

This application claims priority from provisional U.S. application Serial No. 60/225,590, filed Aug. 16, 2000, incorporated herein by reference in its entirety.

FIELD OF THE INVENTION

The present invention relates to crystalline polymorphic forms of a highly potent epothilone analog that is characterized by enhanced properties.

BACKGROUND OF THE INVENTION

Epothilones are macrolide compounds that find utility in the pharmaceutical field. For example, Epothilones A and B having the structures:

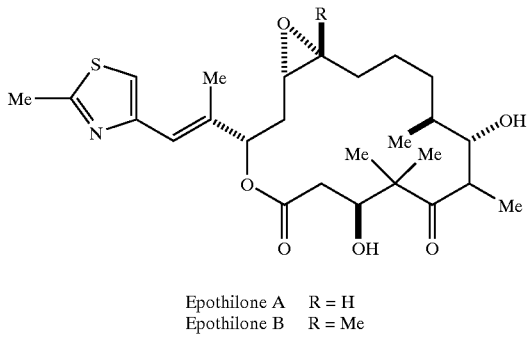

Epothilone A  R = H
Epothilone B  R = Me may be found to exert microtubule-stabilizing effects similar to paclitaxel (TAXOL®) and hence cytotoxic activity against rapidly proliferating cells, such as, tumor cells or other hyperproliferative cellular disease, see Hofle, G., et al., *Angew. Chem. Int. Ed. Engl.*, Vol. 35, No.13/14, 1567–1569 (1996); WO93/10121 published May 27, 1993; and WO97/19086 published May 29, 1997.

Various epothilone analogs have been synthesized and may be used to treat a variety of cancers and other abnormal proliferative diseases. Such analogs are disclosed in Hofle et al., *Id.*; Nicolaou, K. C., et al., *Angew Chem. Int. Ed. Engl.* Vol. 36, No. 19, 2097–2103 (1997); and Su, D.-S., et al., *Angew Chem. Int. Ed. Engl.*, Vol. 36, No. 19, 2093–2097 (1997).

A particularly advantageous epothilone analog that has been found to have advantageous activity is [1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione. In accordance with the present invention, two crystal forms of the subject epothilone analog are provided. These polymorphs, which have been designated as Forms A and B, respectively, are novel crystal forms and are identified hereinbelow.

SUMMARY OF THE INVENTION

Figure 1:
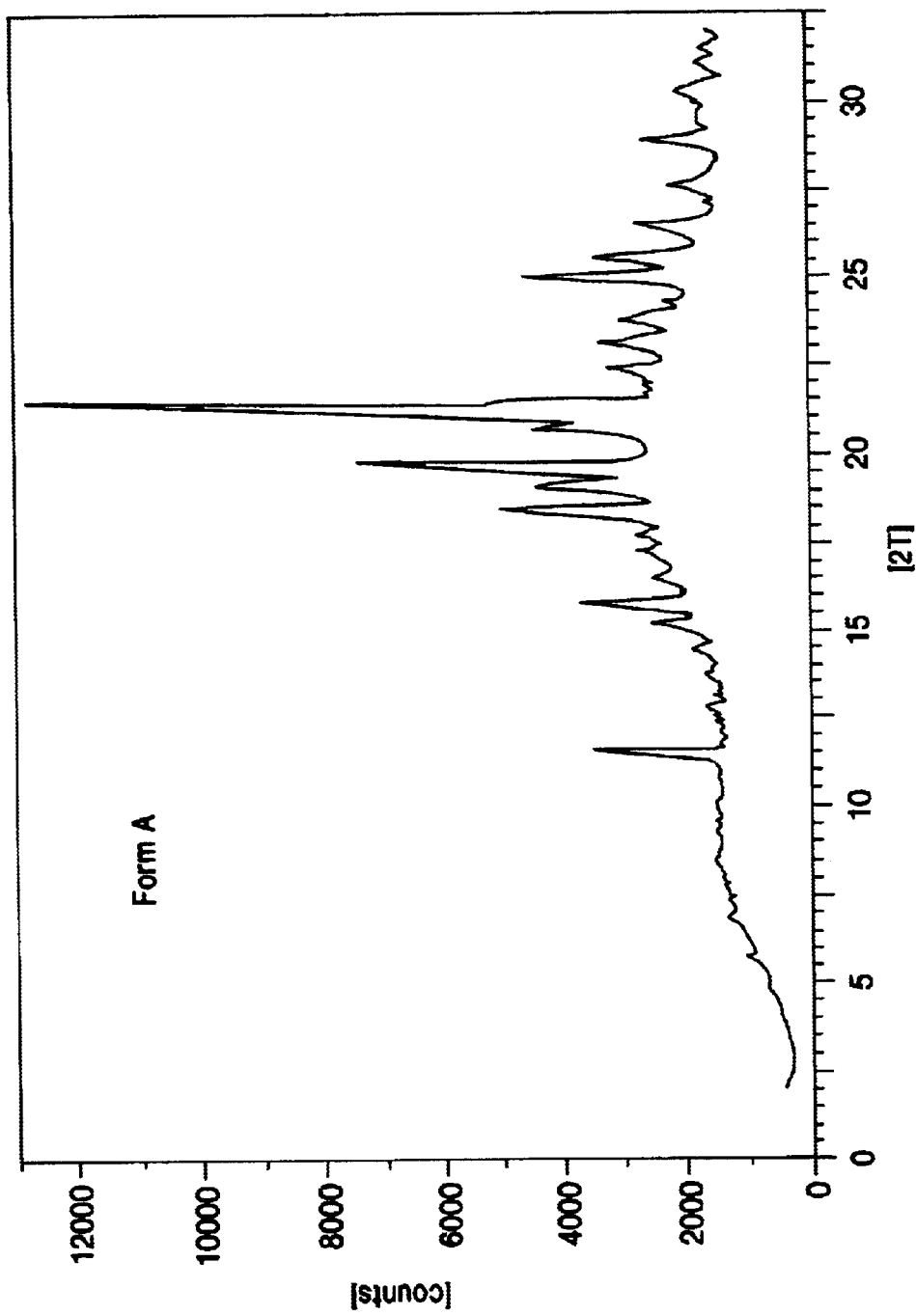
FIG. 1 is a powder x-ray diffraction pattern (CuKα λ=1.5406 Å at room temperature) of Form A of the subject epothilone analog.

In accordance with the present invention, there are provided two crystalline polymorphs of the epothilone analog represented by formula I.

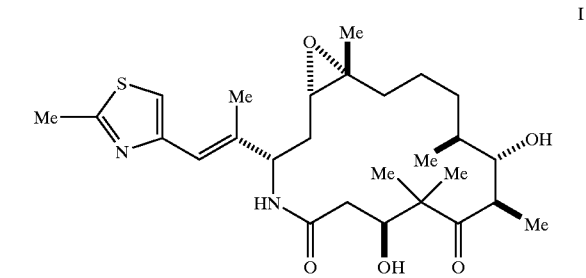

One of these polymorphs, designated Form A, has been found to have particularly advantageous properties. The present invention is directed to crystalline polymorphs Form A and Form B as well as mixtures thereof. The present invention further pertains to the use of these crystalline forms in the treatment of cancers and other proliferating diseases and pharmaceutical formulations containing them.

DETAILED DESCRIPTION OF THE INVENTION

In accordance with the present invention, there are provided polymorphs of an epothilone analog represented by formula I below

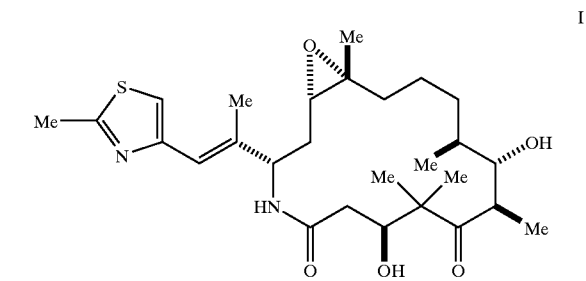

The epothilone analog represented by formula I chemically is [1S-[1R*,3R*(E),7R*,10S*, 11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione. This analog and the preparation thereof are described in U.S. patent application Ser. No. 09/170,582, filed Oct. 13, 1998, the disclosure of which is incorporated herein by reference. The polymorphs of the analog represented by formula I above are microtubule-stabilizing agents. They are thus useful in the treatment of a variety of cancers and other proliferative diseases including, but not limited to, the following;

carcinoma, including that of the bladder, breast, colon, kidney, liver, lung, ovary, pancreas, stomach, cervix, thyroid and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, teratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma.

The subject polymorphs will also inhibit angiogenesis, thereby affecting the growth of tumors and providing treatment of tumors and tumor-related disorders. Such anti-angiogenesis properties will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

The polymorphs of the analog represented by formula I will induce or inhibit apoptosis, a physiological cell death process critical for normal development and homeostasis. Alterations of apoptotic pathways contribute to the pathogenesis of a variety of human diseases. The subject polymorphs, as modulators of apoptosis, will be useful in the treatment of a variety of human diseases with aberrations in apoptosis including, but not limited to, cancer and precancerous lesions, immune response related diseases, viral infections, degenerative diseases of the musculoskeletal system and kidney disease.

Without wishing to be bound to any mechanism or morphology, the such crystalline forms of the epothilone analog represented by formula I may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

The effective amount of the subject polymorphs, particularly Form A, may be determined by one of ordinary skill in the art, and includes exemplary dosage amounts for a human of from about 0.05 to 200 mg/kg/day, which may be administered in a single dose or in the form of individual divided doses, such as from 1 to 4 times per day. Preferably, the subject polymorphs are administered in a dosage of less than 100 mg/kg/day, in a single dose or in 2 to 4 divided doses. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. The subject polymorphs are preferably administered parenterally, however, other routes of administration are contemplated herein as are recognized by those skill in the oncology arts. Preferred subjects for treatment include animals, most preferably mammalian species such as humans, and domestic animals such as dogs, cats and the like, subject to the aforementioned disorders.

The preparation of the epothilone analogs represented by formula I described in U.S. patent application Ser. No. 09/170,582 produced the subject epothilone analog as an oil that can be chromatographed and purified to yield an amorphous powder. A preferred preparation is described in a continuing application under Ser. No. 09/528,526 filed on Mar. 20, 2000, the disclosure of which is incorporated herein by reference. In this preparation, as pertains to the analogs represented by formula I, epothilone B is reacted with an azide donor agent and a buffering agent in the presence of a palladium catalyst and a reducing agent to form an intermediate represented by the formula

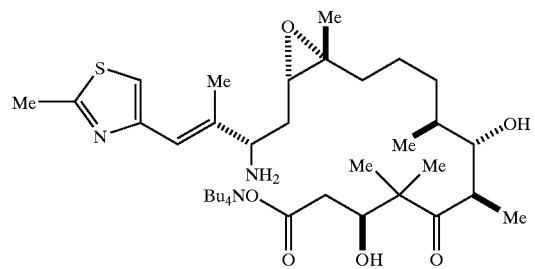

A macrolactamization reaction is then carried out on the intermediate to form the analog represented by formula I. It has now been found that this analog, in its crystalline form, consists of a mixture of Forms A and B as fully described herein. The amorphous form of the epothilone analog represented by formula I can be taken up in a suitable solvent, preferably a mixed solvent such as ethyl acetate/dichloromethane/triethylamine, purified such as by silica gel pad filtration, and crystallized by cooling to a temperature of about 5° C. to form a crystalline material that is a mixture of Form A and Form B. The purification step using a solvent mixture containing a component such as dichloromethane removes residual solvents from the synthesis that could interfere with the crystallization process.

Generally, taking the purified material in a limited amount of ethyl acetate and heating the resultant slurry to about 75–80° C. will cause the formation of Form A. By limited amount is meant from about 8 to 16 mL, preferably from about 8 to 12 mL, of ethyl acetate per gram of purified material. As the solution is heated, a thin slurry forms which has been found to be predominately Form B. At about 75° C. the slurry undergoes a material thickening which has been found to be the formation of Form A. The slurry is held at about 75–80° C. for about an hour to assure completion of the formation of Form A at which time cyclohexane is added to the slurry in a ratio to ethyl acetate of from about 1:2 to 2:2, preferably about 1:2, and the mixture is allowed to cool to ambient temperature at which it is maintained with stirring for a period of from about 12 to 96 hours. The mixture is then cooled to about 5° C. over about two hours after which the crystals of Form A of the subject epothilone analog are recovered. Form A is afforded in good yield and purity.

Alternate procedures for the preparation of Form A involve the addition of seed crystals. In the descriptions that follow, seed crystals of Form A were used, but seed crystals of Form B, or mixtures thereof can be used as well. In one such procedure, the purified material is taken up in a limited amount of ethyl acetate as described above and heated to about 75° C., seed crystals are added and the mixture maintained for about 30 minutes. An amount of cyclohexane as described above is then added dropwise maintaining the temperature at about 70° C. The mixture is thereafter cooled to 20° C. and held with stirring for 18 hours after which it is cooled to 5° C. and the white crystals of Form A recovered by physical separation, e.g. filtration.

In a second procedure, the initial solution of material in ethyl acetate is heated to 75° C. for at least an hour until a solution is produced. The solution is cooled to about 50° C. over the course of about two hours adding seed crystals of Form A when the temperature reaches about 60° C. Crystals begin to appear at about 55° C. The temperature is again reduced to about 20° C. over a further two hours during one hour of which an amount of cyclohexane as described above is added dropwise. The final slurry is further cooled over two hours to −10° C. and held at that temperature for an additional hour. The slurry is then filtered to afford white crystals of Form A.

In a further alternate procedure, the material is taken up in a larger amount, i.e. at least about 40 mL/g of ethyl acetate and the resultant slurry heated to about 80° C. until a solution is formed which is then cooled to about 70° C. over the course of about one hour. Seed crystals of Form A are added when the solution temperature reaches about 70° C. The temperature is then reduced to about 30° C. over a further three hours. Crystals begin to appear at about 65° C. The temperature is reduced to −10° C. over an additional three hours during a thirty minute period thereof a quantity of cyclohexane as described above is added dropwise. The temperature is maintained at −10° C. for a further hour. The final slurry is filtered to afford white crystals of Form A. The yield and purity of Form A by these procedures is considered very good.

Form B of the subject epothilone analogs represented by Formula I above is obtained by forming a slurry of the crude material in a larger quantity of ethyl acetate, i.e. from about 40 to 50 mL per g., and heating at 70° C. to 80° C. for an hour to form a solution which is then held at temperature for about thirty minutes. The solution is cooled to about 30° C. over the course of about two hours, crystals beginning to appear at about 38° C. The temperature is further reduced to about −10° C. over one hour during which a quantity of cyclohexane as described above is added dropwise over a period of thirty minutes. The final slurry is held at −10° C. over a further two hours and filtered to afford white crystals of Form B.

In an alternative preparation to that above, the crude material is slurried with a like quantity of ethyl acetate and heated to about 78° C. to form a solution that is then held at temperature for about thirty minutes. The solution is cooled to about 10° C. over the course of about two hours and seed crystals of Form A are added when the temperature reaches about 10° C. The temperature is again reduced over a further two hours to −10° C. during a thirty minute period thereof an amount of cyclohexane as described above is added dropwise. The temperature is maintained at −10° C. for two hours. The final slurry is filtered to afford white crystals of Form B.

In a further alternate procedure, the purified material is taken up in another solvent, preferably toluene, in an amount between about 10 and 20 mL per g., and heated to 75° C. to 80° C. for 30 minutes and then allowed to cool to 20° C. and maintained for 18 hours with stirring. White crystals of Form B are recovered from the slurry by physical separation. The yield and purity of Form B by these procedures is considered very good.

Figure 2:
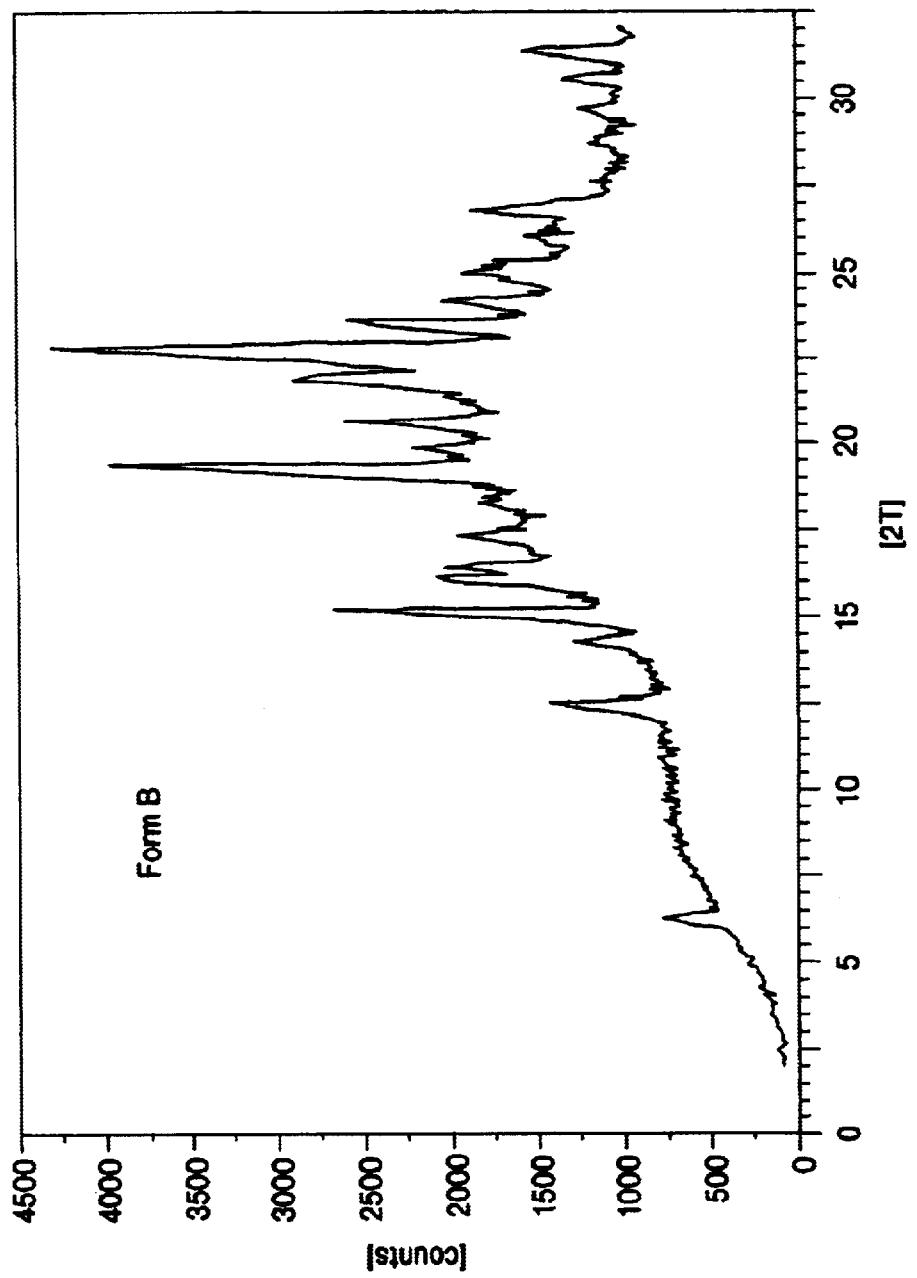
FIG. 2 is a powder x-ray diffraction pattern of Form B (Cu Kα λ=1.5406 Å at room temperature) of the subject epothilone analog.
Figure 3:
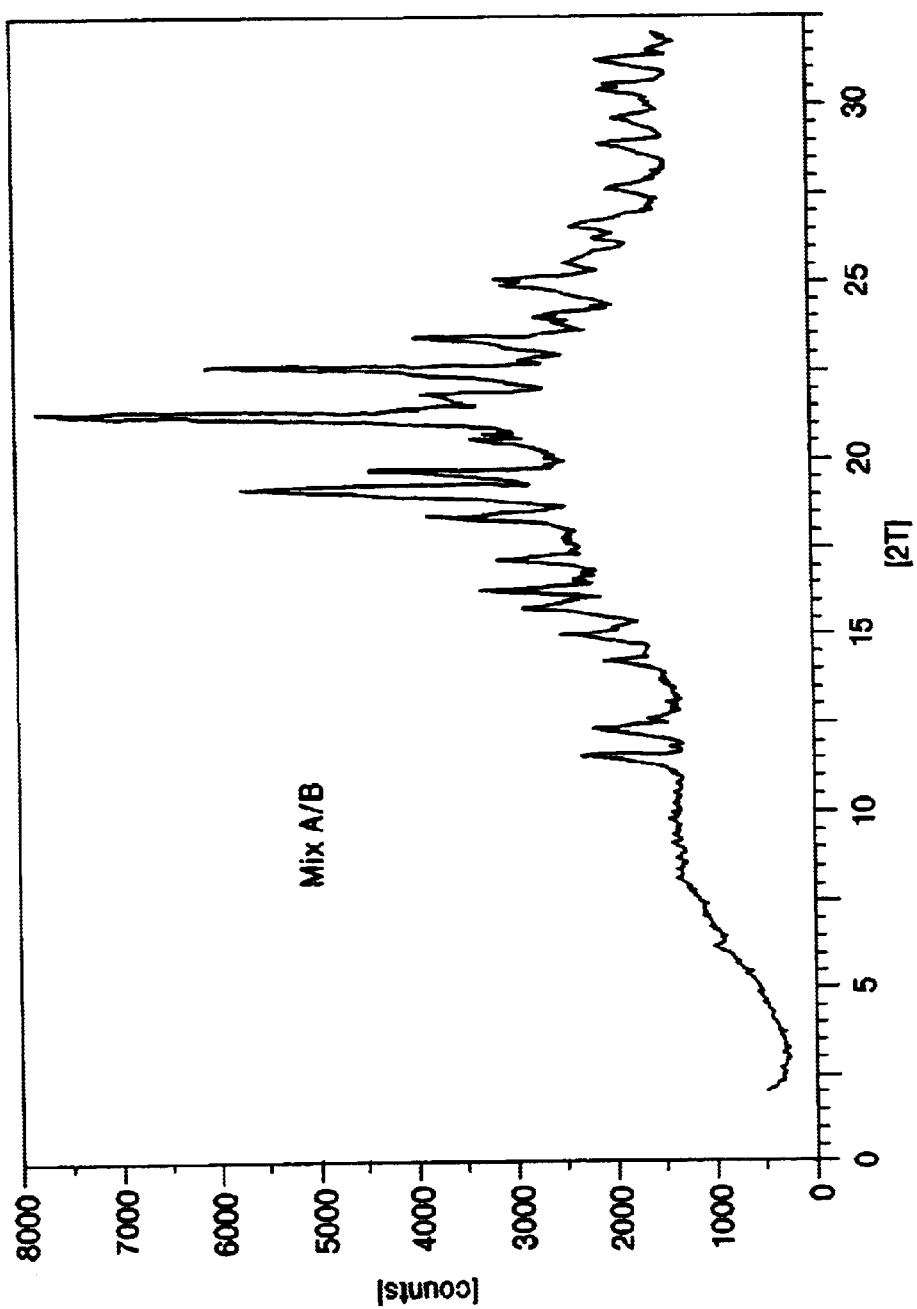
FIG. 3 is a powder x-ray diffraction pattern of a mixture of Forms A and B (Cu Kα λ=1.5406 Å at room temperature) of the subject epothilone analog.
Figure 4:
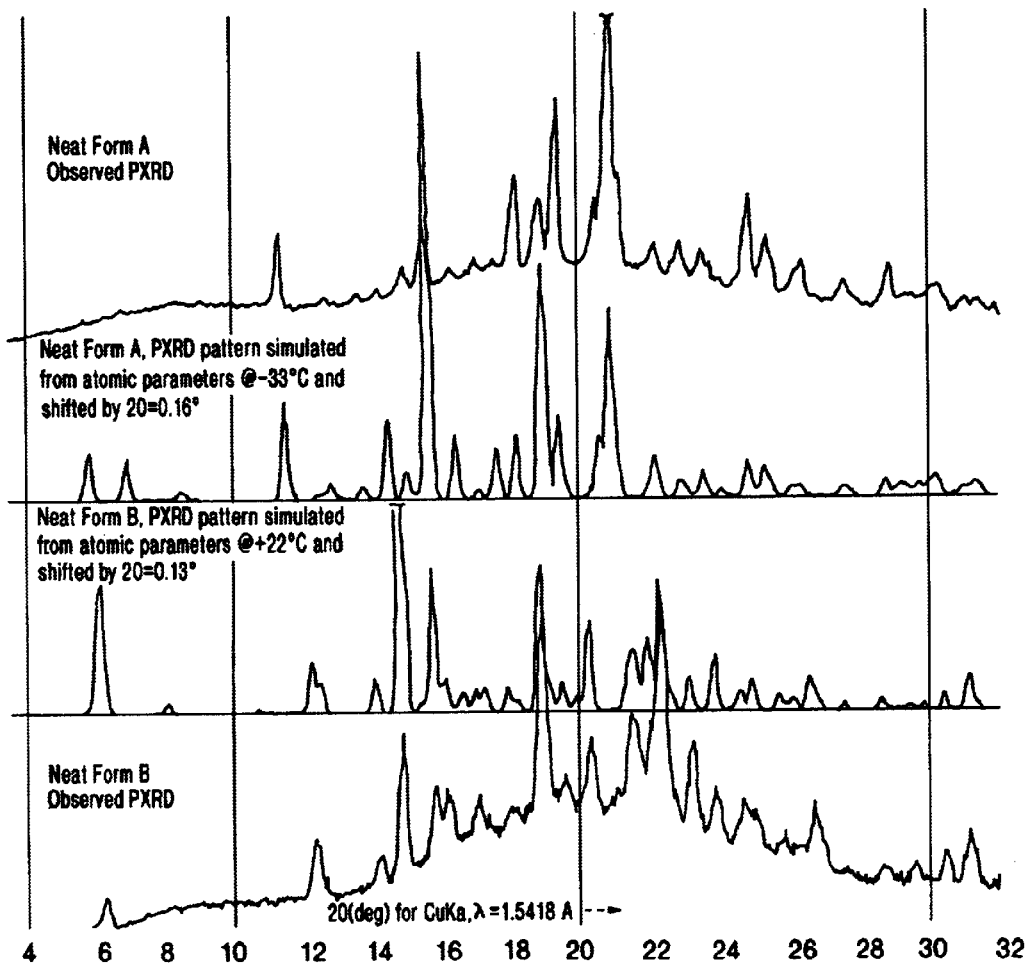
FIG. 4 is a comparison of the simulated and actual powder x-ray diffraction patterns of Forms A and B of the subject epothilone analog.

FIGS. 1 through 3 are powder x-ray diffraction patterns of Forms A, B and a mixture thereof, respectively, of the subject analog. FIG. 4 is a comparison of powder x-ray diffraction patterns simulated from the single crystal structures for Forms A and B with the actual pattern for each. X-ray diffraction patterns were generated from a Philips Xpert with a generator source of 44 kV and 40 mA and a CuKα filament of λ=1.5406 Å at room temperature. In the results shown in FIGS. 1–4, as well as in Tables 1 and 2 below which contain the data in summary form, the differences clearly establish that Forms A and B of the subject epothilone analog possess different crystalline structures. In the Tables, Peak Intensities of from 1 to 12 are classified as very weak, from 13 to 32 as weak, from 33 to 64 as average, from 65 to 87 as strong and from 88 to 100 as very strong.

TABLE 1

| Values for Form A | |
|---|---|
| Peak Position (two theta) (CuKα λ = 1.5406 Å at room temperature) | Relative Peak Intensity |
| 5.69 | Very weak |
| 6.76 | Very weak |
| 8.38 | Very weak |
| 11.43 | Weak |
| 12.74 | Very weak |
| 13.62 | Very weak |
| 14.35 | Very weak |
| 15.09 | Very weak |
| 15.66 | Weak |
| 16.43 | Very weak |
| 17.16 | Very weak |
| 17.66 | Very weak |
| 18.31 | Weak |
| 19.03 | Weak |
| 19.54 | Average |
| 20.57 | Weak |
| 21.06 | Very strong |
| 21.29 | Weak |
| 22.31 | Weak |
| 23.02 | Weak |
| 23.66 | Weak |
| 24.18 | Very weak |
| 24.98 | Weak |
| 25.50 | Weak |
| 26.23 | Very weak |
| 26.46 | Very weak |
| 27.59 | Very weak |
| 28.89 | Very weak |

TABLE 1-continued

Values for Form A

| Peak Position (two theta) (CuKα λ = 1.5406 Å at room temperature) | Relative Peak Intensity |
|---|---|
| 29.58 | Very weak |
| 30.32 | Very weak |
| 31.08 | Very weak |
| 31.52 | Very weak |

TABLE 2

Values for Form B

| Peak Position (two theta) (CuKα λ = 1.5406 Å at room temperature) | Relative Peak Intensity |
|---|---|
| 6.17 | Very weak |
| 10.72 | Very weak |
| 12.33 | Weak |
| 14.17 | Weak |
| 14.93 | Average |
| 15.88 | Average |
| 16.17 | Average |
| 17.11 | Average |
| 17.98 | Weak |
| 19.01 | Very strong |
| 19.61 | Average |
| 20.38 | Average |
| 21.55 | Average |
| 21.73 | Average |
| 22.48 | Very strong |
| 23.34 | Average |
| 23.93 | Average |
| 24.78 | Average |
| 25.15 | Weak |
| 25.90 | Weak |
| 26.63 | Average |
| 27.59 | Very weak |
| 28.66 | Weak |
| 29.55 | Weak |
| 30.49 | Weak |
| 31.22 | Weak |

Figure 5:
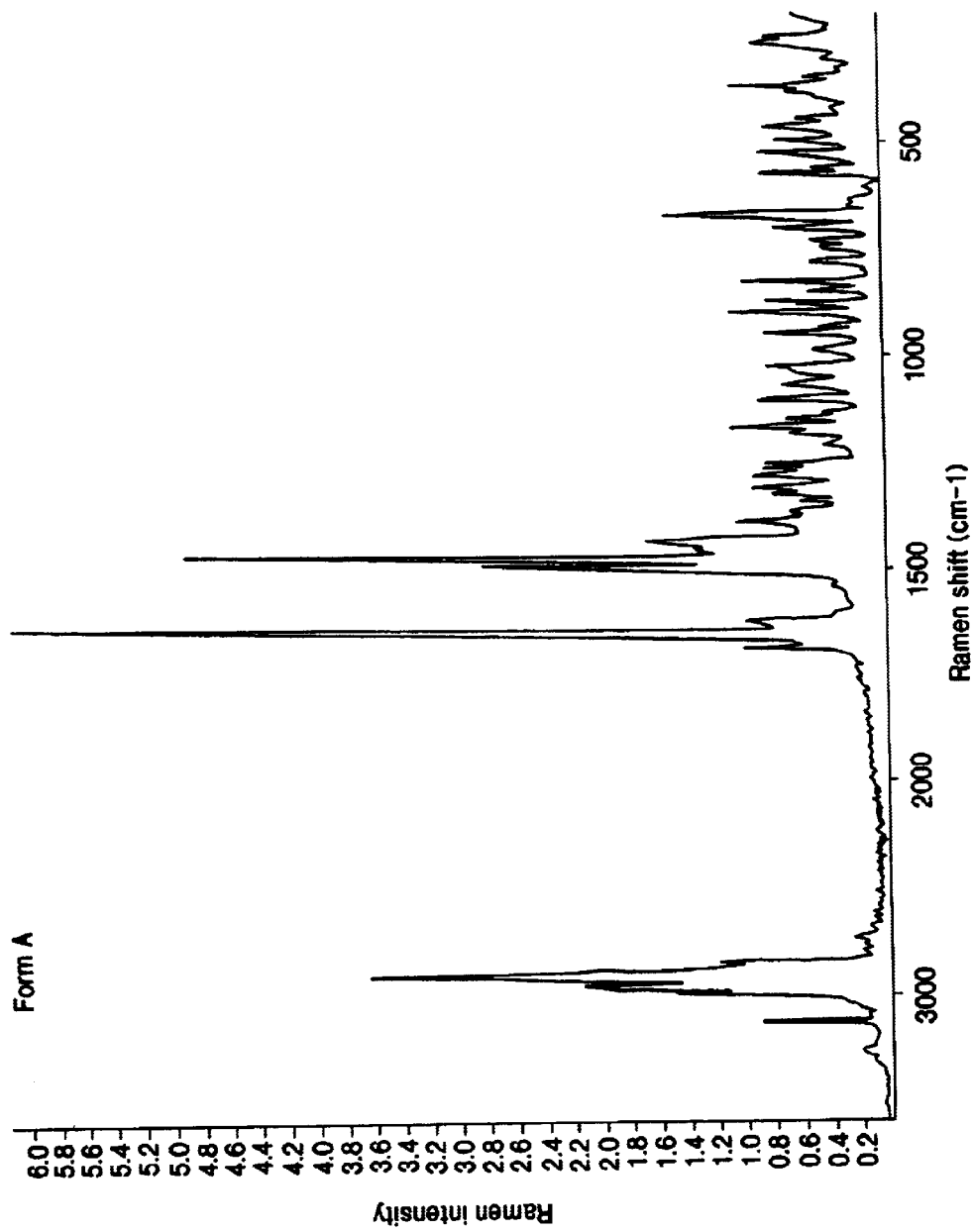
FIG. 5 is a Raman spectrum of Form A of the subject epothilone analog.
Figure 6:
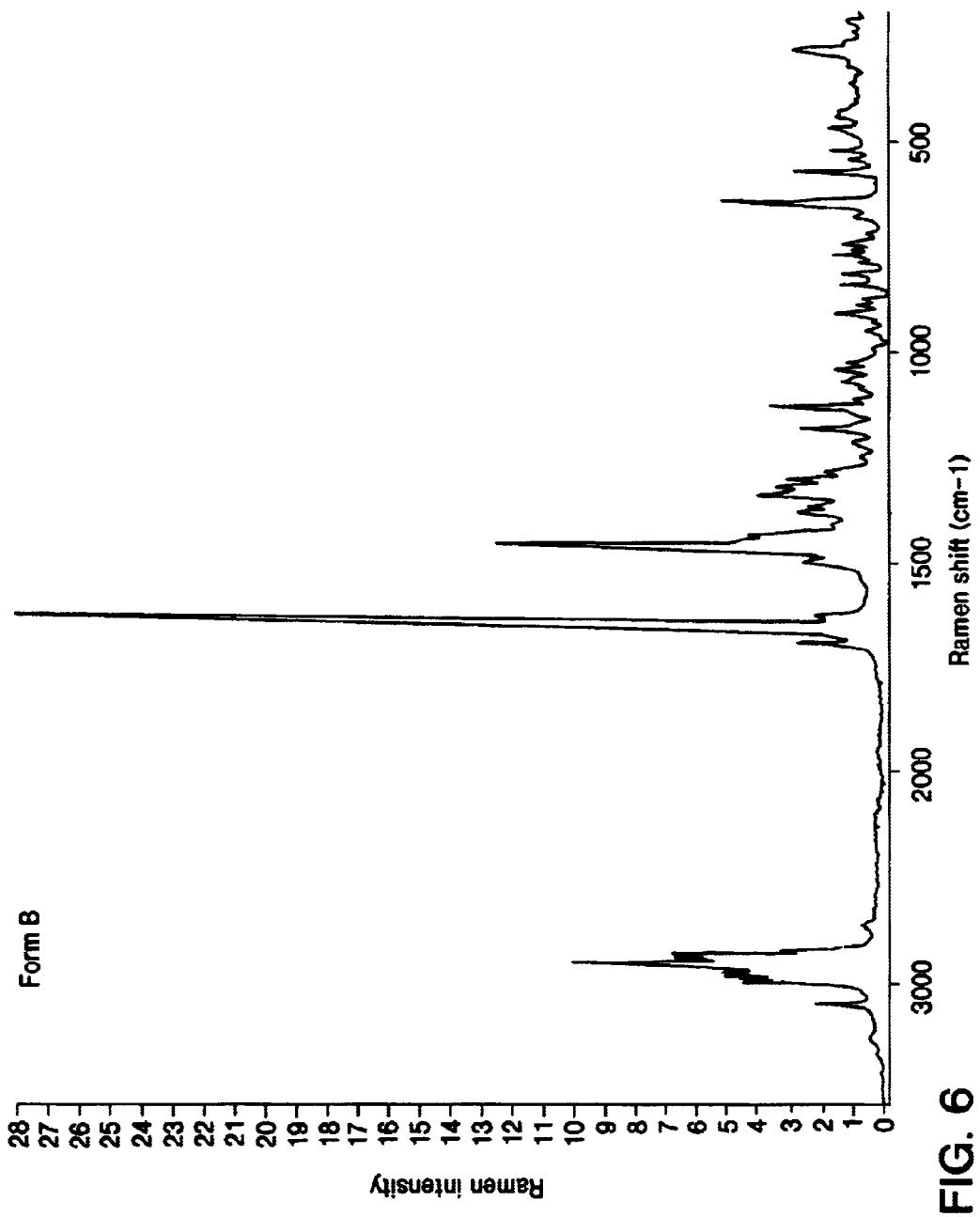
FIG. 6 is a Raman spectrum of Form B of the subject epothilone analog.
Figure 7:
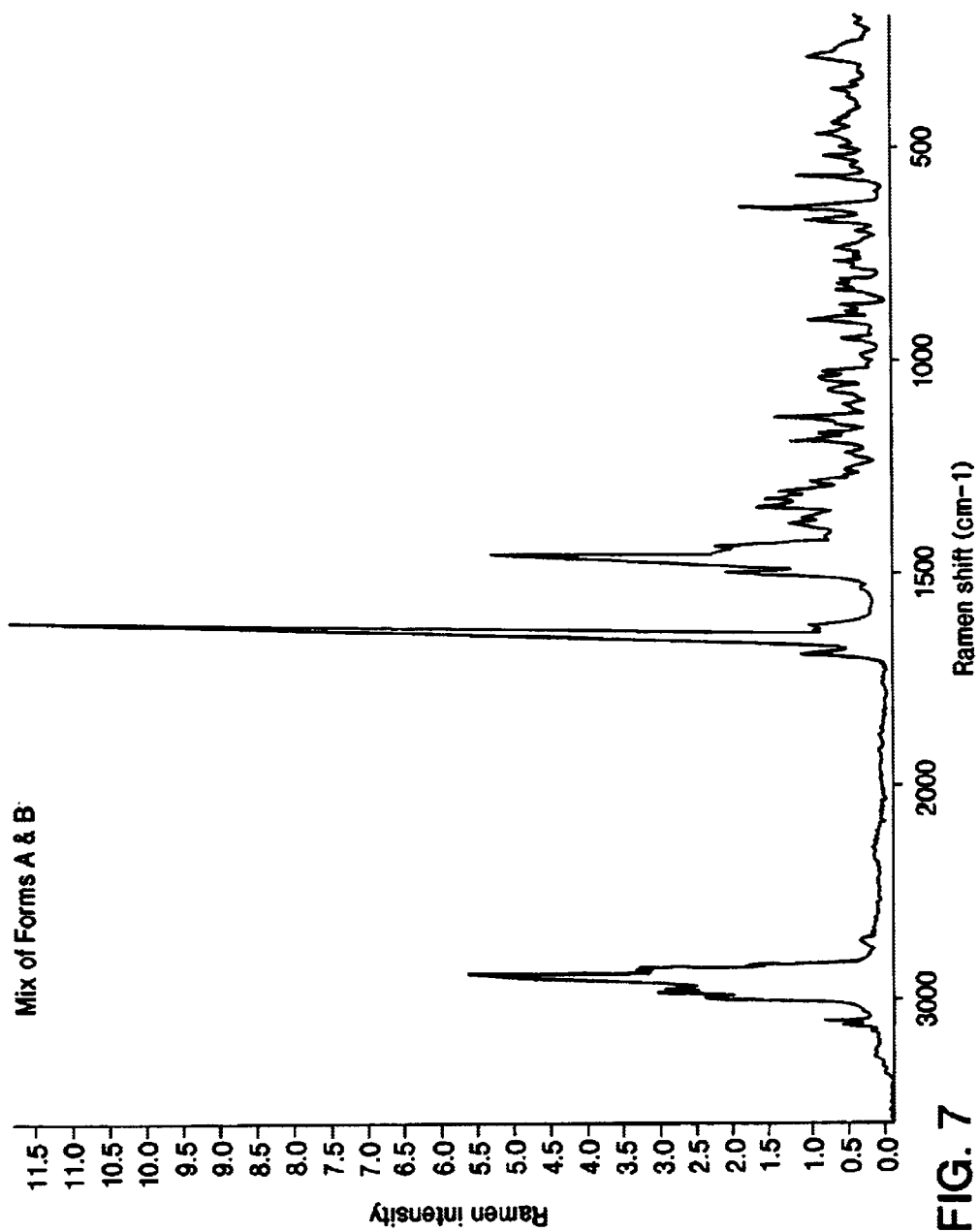
FIG. 7 is a Raman spectrum of a mixture of Forms A and B of the subject epothilone analog.

FIGS. 5 through 7 are the results of Raman spectroscopy of Forms A, B and a mixture thereof, respectively, of the subject analog. The spectra also demonstrate two distinct crystal forms, in particular the bands at 3130 cm-1 and 3115 cm-1.

Distinguishing physical characteristics of the two polymorph forms are shown in Table 3 below. Solution calorimetry was determined using a Thermometrics Microcalorimeter in ethanol at 25° C. The solubilities were likewise determined at 25° C. It is further evident from certain of the data, particularly the heat of solution, that Form A is the more stable and, therefore, Form A is preferred.

TABLE 3

| Characteristic | Form A | Form B |
|---|---|---|
| Solubility in Water | 0.1254 | 0.1907 |
| Solubility in 3% Polysorbate 80 (Aqueous) | 0.2511 | 0.5799 |
| Heat of Solution | 20.6 kJ/mol | 9.86 kJ/mol |

Form A and Form B of the epothilone analogs represented by formula I above can be further characterized by unit cell parameters obtained from single crystal X-ray crystallographic analysis as set forth below. A detailed account of unit cells can be found in Chapter 3 of Stout & Jensen, *X-Ray structure Determination: A Practical Guide*, MacMillian Co., New York, N.Y. (1968).

| | Unit Cell Parameters of Form A | Unit Cell Parameters of Form B |
|---|---|---|
| Cell dimensions | a = 14.152(6) Å<br>b = 30.72(2) Å<br>c = 6.212(3) Å<br>Volume = 2701(4) A$^3$ | a = 16.675(2) Å<br>b = 28.083(4) Å<br>c = 6.054(1) Å<br>Volume = 2835(1) A$^3$ |
| Space group | P2$_1$2$_1$2$_1$<br>Orthorhombic | P2$_1$2$_1$2$_1$<br>Orthorhombic |
| Molecules/unit cell | 4 | 4 |
| Density (calculated) (g/cm$^3$) | 1.247 | 1.187 |
| Melting point | 182–185° C. (decompostion) | 191–199° C. (decompostion) |

Figure 8:
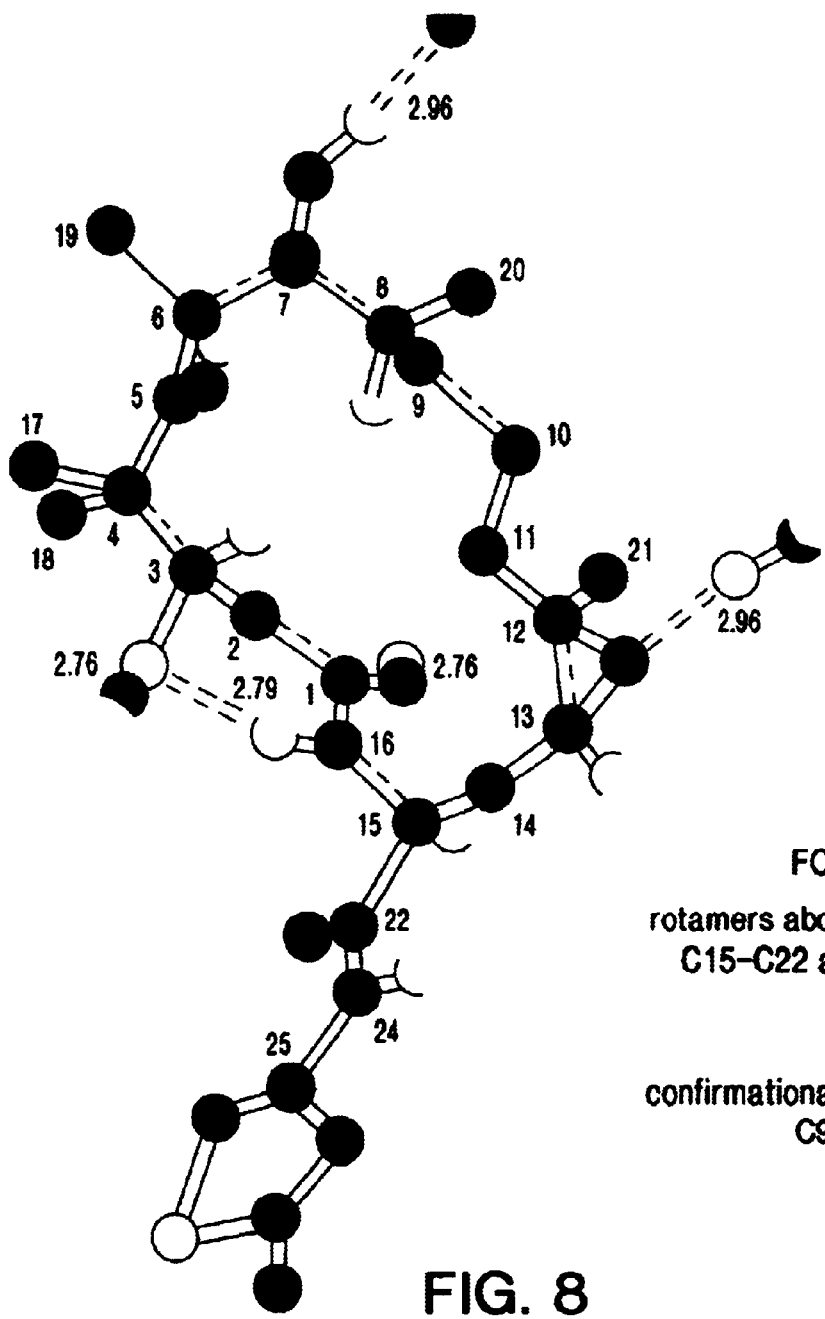
FIG. 8 depicts the solid state conformation in Form A of the subject epothilone analog.
Figure 9:
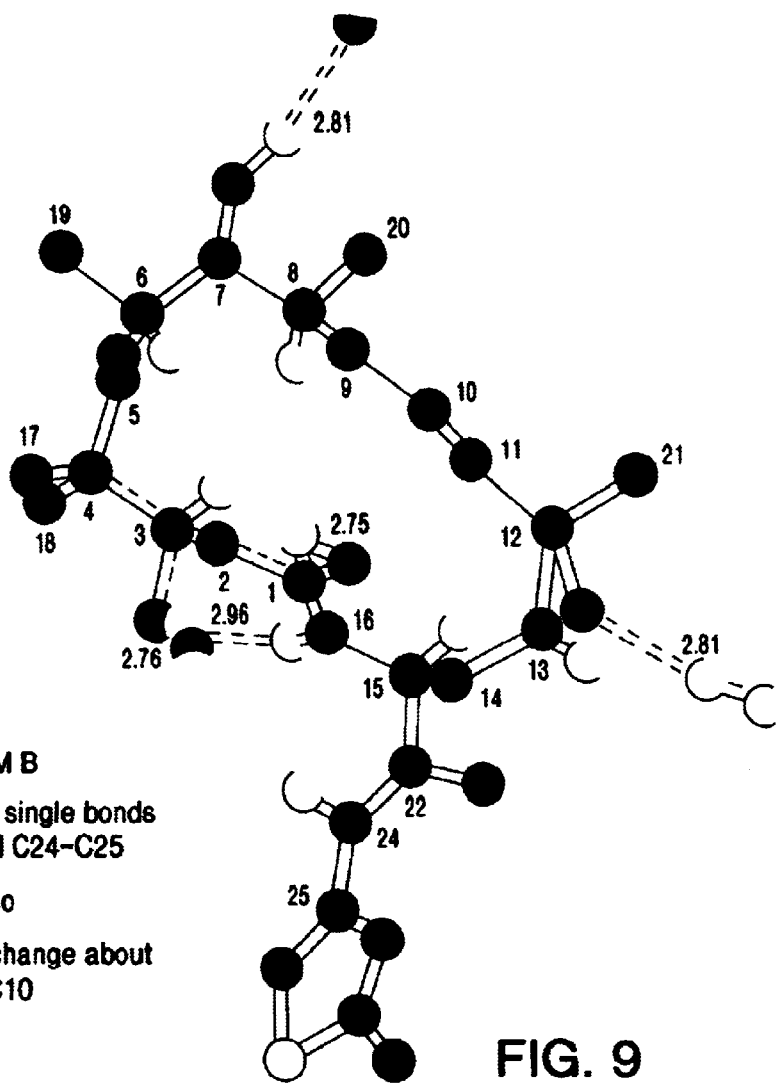
FIG. 9 depicts the solid state conformation in Form B of the subject epothilone analog.

The differences between Forms A and B of the subject epothilone analog are further illustrated by the solid state conformations of each as illustrated in FIG. 8 and FIG. 9, respectively, based on the fractional atomic coordinates listed in Tables 4 through 7 below.

TABLE 4

Fractional Atomic Coordinates for the Epothilone Analog of Formula I: Form A

| Atom | X | Y | Z | U11*10e2 | U22*10e2 | U33*10e2 | U12*10e2 | U13*10e2 | U23*10e2 |
|---|---|---|---|---|---|---|---|---|---|
| C1 | 0.3879(3) | 0.4352(1) | 0.5503(9) | 60(6) | 25(4) | 138(8) | −2(4) | 16(5) | −9(4) |
| O1 | 0.4055(2) | 0.4300(1) | 0.7435(5) | 68(4) | 85(4) | 100(5) | 6(3) | 4(3) | 1(3) |
| C2 | 0.2864(3) | 0.4340(1) | 0.4675(7) | 42(6) | 64(5) | 106(6) | 0(4) | 3(4) | −5(4) |
| C3 | 0.2696(3) | 0.4210(1) | 0.2325(7) | 56(6) | 44(5) | 103(6) | −7(4) | 5(4) | 13(4) |
| O3 | 0.3097(2) | 0.4550(1) | 0.1027(5) | 71(4) | 58(3) | 128(4) | −6(3) | 18(3) | 3(3) |
| C4 | 0.1615(3) | 0.4154(1) | 0.1852(7) | 50(6) | 63(5) | 112(6) | −12(4) | −3(4) | 7(4) |
| C5 | 0.1289(3) | 0.3732(1) | 0.2895(8) | 58(6) | 82(5) | 103(7) | −6(4) | −13(5) | 4(5) |
| O5 | 0.0935(3) | 0.3748(1) | 0.4713(6) | 135(6) | 83(4) | 144(5) | −16(4) | 39(4) | 5(3) |
| C6 | 0.1343(3) | 0.3296(1) | 0.1769(8) | 66(6) | 71(5) | 118(6) | −13(5) | −7(4) | −10(4) |
| C7 | 0.1503(3) | 0.2921(1) | 0.3353(8) | 84(6) | 43(5) | 134(6) | −27(4) | −2(5) | −10(5) |
| O7 | 0.1410(3) | 0.2528(1) | 0.2127(6) | 127(6) | 61(4) | 163(5) | −34(3) | −17(4) | −9(3) |
| C8 | 0.2449(4) | 0.2936(1) | 0.4540(8) | 83(7) | 56(5) | 127(6) | −26(5) | −4(5) | 3(5) |
| C9 | 0.3284(4) | 0.2824(1) | 0.3072(9) | 81(7) | 68(5) | 153(7) | −1(5) | −4(5) | −26(5) |
| C10 | 0.4258(4) | 0.2877(1) | 0.4141(8) | 76(7) | 56(5) | 166(8) | 13(5) | −19(5) | −15(5) |
| C11 | 0.4467(3) | 0.3359(1) | 0.4622(8) | 67(6) | 61(5) | 126(7) | −3(4) | −19(4) | −5(5) |
| C12 | 0.5220(3) | 0.3426(1) | 0.6294(8) | 53(6) | 64(5) | 138(7) | 16(4) | 8(5) | −1(5) |
| O12 | 0.6171(2) | 0.3288(1) | 0.5612(5) | 56(4) | 61(3) | 155(4) | 15(3) | 8(3) | 4(3) |

TABLE 4-continued

Fractional Atomic Coordinates for the Epothilone Analog of Formula I: Form A

| Atom | X | Y | Z | U11*10e2 | U22*10e2 | U33*10e2 | U12*10e2 | U13*10e2 | U23*10e2 |
|---|---|---|---|---|---|---|---|---|---|
| C13 | 0.5983(3) | 0.3746(1) | 0.5991(8) | 50(6) | 45(5) | 162(7) | 3(4) | 2(5) | −8(5) |
| C14 | 0.6099(3) | 0.4053(1) | 0.4113(8) | 47(6) | 63(5) | 159(7) | 2(4) | 5(5) | 7(5) |
| C15 | 0.5568(3) | 0.4477(1) | 0.4538(8) | 44(6) | 44(5) | 143(6) | −4(4) | 7(4) | −1(4) |
| N16 | 0.4552(3) | 0.4426(1) | 0.4005(6) | 41(5) | 65(4) | 106(5) | −3(3) | 6(3) | −2(3) |
| C17 | 0.1482(4) | 0.4138(2) | −0.0603(8) | 103(7) | 128(7) | 104(7) | −29(6) | −10(5) | 18(5) |
| C18 | 0.1043(4) | 0.4539(1) | 0.2734(8) | 62(6) | 67(5) | 164(7) | 17(5) | 9(5) | 12(5) |
| C19 | 0.0386(4) | 0.3232(2) | 0.0572(10) | 92(8) | 115(7) | 217(10) | −17(6) | −70(7) | −19(7) |
| C20 | 0.2404(5) | 0.2630(2) | 0.6482(10) | 145(9) | 114(7) | 158(8) | −34(6) | −20(6) | 47(6) |
| C21 | 0.4974(4) | 0.3301(2) | 0.8563(9) | 109(8) | 92(6) | 131(7) | 19(5) | 10(5) | 8(5) |
| C22 | 0.5935(4) | 0.4860(1) | 0.3281(8) | 48(6) | 63(5) | 122(6) | 6(4) | 4(5) | −1(5) |
| C23 | 0.5989(4) | 0.4815(2) | 0.0875(8) | 132(8) | 78(6) | 116(7) | −7(5) | 12(5) | −13(5) |
| C24 | 0.6154(3) | 0.5222(1) | 0.4376(8) | 59(6) | 55(5) | 132(6) | −6(4) | 9(5) | 7(5) |
| C25 | 0.6392(3) | 0.5656(1) | 0.3573(8) | 61(6) | 65(5) | 127(7) | −12(4) | 8(5) | 5(5) |
| N26 | 0.6786(3) | 0.5941(1) | 0.5076(6) | 75(6) | 58(5) | 129(5) | −9(4) | 4(4) | −5(4) |
| C27 | 0.6902(3) | 0.6325(2) | 0.4255(8) | 59(6) | 69(6) | 128(6) | 9(4) | 2(5) | 7(5) |
| S28 | 0.6529(1) | 0.6381(1) | 0.1655(2) | 92(2) | 79(1) | 163(2) | −10(1) | −3(1) | 20(1) |
| C29 | 0.6196(4) | 0.5846(2) | 0.1632(9) | 85(7) | 78(6) | 161(8) | −13(5) | −9(6) | 3(6) |
| C30 | 0.7292(4) | 0.6703(2) | 0.5523(10) | 106(8) | 75(6) | 186(8) | −29(5) | −5(6) | −10(6) |

TABLE 5

Hydrogen Positions: Form A

| Atom | X | Y | Z | U*10E2 |
|---|---|---|---|---|
| H21 | 0.2475(0) | 0.4114(0) | 0.5659(0) | 4.86(0) |
| H22 | 0.2576(0) | 0.4663(0) | 0.4871(0) | 4.86(0) |
| H31 | 0.3056(0) | 0.3905(0) | 0.2005(0) | 4.59(0) |
| H3 | 0.3433(0) | 0.4414(0) | −0.0241(0) | 5.55(0) |
| H61 | 0.1951(0) | 0.3304(0) | 0.0646(0) | 5.55(0) |
| H71 | 0.0960(0) | 0.2932(0) | 0.4607(0) | 5.80(0) |
| H7 | 0.1332(0) | 0.2276(0) | 0.3158(0) | 7.23(0) |
| H81 | 0.2588(0) | 0.3266(0) | 0.5107(0) | 5.85(0) |
| H91 | 0.3274(0) | 0.3037(0) | 0.1672(0) | 6.41(0) |
| H92 | 0.3217(0) | 0.2491(0) | 0.2527(0) | 6.41(0) |
| H101 | 0.4802(0) | 0.2743(0) | 0.3130(0) | 6.34(0) |
| H102 | 0.4253(0) | 0.2697(0) | 0.5663(0) | 6.34(0) |
| H111 | 0.4687(0) | 0.3519(0) | 0.3132(0) | 5.60(0) |
| H112 | 0.3823(0) | 0.3519(0) | 0.5172(0) | 5.60(0) |
| H131 | 0.6275(0) | 0.3905(0) | 0.7410(0) | 5.60(0) |
| H141 | 0.6837(0) | 0.4117(0) | 0.3814(0) | 5.88(0) |
| H142 | 0.5803(0) | 0.3901(0) | 0.2659(0) | 5.88(0) |
| H151 | 0.5638(0) | 0.4542(0) | 0.6281(0) | 5.35(0) |
| H16 | 0.4353(0) | 0.4447(0) | 0.2429(0) | 4.88(0) |
| H171 | 0.1722(0) | 0.4437(0) | −0.1367(0) | 6.90(0) |
| H172 | 0.1919(0) | 0.3871(0) | −0.1308(0) | 6.90(0) |
| H173 | 0.0763(0) | 0.4077(0) | −0.1076(0) | 6.90(0) |
| H181 | 0.1273(0) | 0.4835(0) | 0.1956(0) | 6.31(0) |
| H182 | 0.0295(0) | 0.4491(0) | 0.2355(0) | 6.31(0) |
| H183 | 0.1123(0) | 0.4566(0) | 0.4436(0) | 6.31(0) |
| H191 | 0.0370(0) | 0.2923(0) | −0.0226(0) | 8.78(0) |
| H192 | −0.0186(0) | 0.3233(0) | 0.1794(0) | 8.78(0) |
| H193 | 0.0259(0) | 0.3491(0) | −0.0525(0) | 8.78(0) |
| H201 | 0.3050(0) | 0.2635(0) | 0.7355(0) | 8.17(0) |
| H202 | 0.1828(0) | 0.2733(0) | 0.7536(0) | 8.17(0) |
| H203 | 0.2252(0) | 0.2304(0) | 0.5923(0) | 8.17(0) |
| H211 | 0.4260(0) | 0.3415(0) | 0.8951(0) | 6.84(0) |
| H212 | 0.4998(0) | 0.2955(0) | 0.8754(0) | 6.84(0) |

TABLE 6

Fractional Atomic Coordinates for the Epothilone Analog of Formula I: Form B

| Atom | X | Y | Z | U11*10e2 | U22*10e2 | U33*10e2 | U12*10e2 | U13*10e2 | U23*10e2 |
|---|---|---|---|---|---|---|---|---|---|
| C1 | 0.2316(2) | 0.1043(2) | 0.7342(8) | 56(4) | 74(5) | 86(6) | 5(4) | −6(4) | −16(5) |
| O1 | 0.2321(2) | 0.1159(1) | 0.5376(5) | 131(4) | 88(3) | 74(4) | −24(3) | −13(3) | −7(3) |
| C2 | 0.1812(2) | 0.0623(1) | 0.8106(7) | 62(4) | 85(5) | 68(5) | −7(4) | −6(4) | −22(5) |
| C3 | 0.1535(2) | 0.0622(1) | 1.0506(7) | 52(4) | 67(4) | 71(5) | 1(3) | −19(4) | −6(4) |
| O3 | 0.2226(2) | 0.0539(1) | 1.1856(5) | 65(3) | 123(4) | 96(4) | 7(3) | −29(3) | −19(4) |
| C4 | 0.0876(2) | 0.0237(1) | 1.0903(7) | 63(4) | 75(4) | 63(5) | 5(4) | −4(4) | −10(4) |
| C5 | 0.0096(2) | 0.0415(1) | 0.9838(8) | 57(4) | 61(4) | 78(5) | −7(3) | −2(4) | −10(4) |
| O5 | −0.0132(2) | 0.0252(1) | 0.8117(6) | 100(4) | 103(4) | 100(4) | 19(3) | −38(3) | −38(4) |
| C6 | −0.0409(2) | 0.0796(1) | 1.1023(6) | 53(4) | 77(4) | 92(6) | 14(3) | 2(5) | −17(5) |
| C7 | −0.0754(2) | 0.1151(1) | 0.9373(9) | 60(4) | 111(4) | 185(5) | 40(3) | 22(4) | −10(4) |
| O7 | −0.1316(2) | 0.1434(1) | 1.0606(7) | 79(3) | 74(5) | 106(6) | 4(4) | 8(5) | −14(5) |
| C8 | −0.0135(3) | 0.1468(1) | 0.8213(8) | 75(5) | 69(4) | 136(7) | −10(4) | −1(5) | −19(5) |

TABLE 6-continued

Fractional Atomic Coordinates for the Epothilone Analog of Formula I: Form B

| Atom | X | Y | Z | U11*10e2 | U22*10e2 | U33*10e2 | U12*10e2 | U13*10e2 | U23*10e2 |
|---|---|---|---|---|---|---|---|---|---|
| C9 | 0.0274(2) | 0.1817(1) | 0.9812(9) | 80(5) | 89(5) | 175(8) | −21(4) | 15(7) | −27(6) |
| C10 | 0.0946(3) | 0.2107(2) | 0.8766(10) | 95(5) | 98(6) | 191(9) | −22(5) | 27(7) | −48(7) |
| C11 | 0.1389(3) | 0.2407(2) | 1.0447(11) | 97(5) | 64(5) | 208(9) | −16(5) | 10(7) | −28(6) |
| C12 | 0.2065(3) | 0.2688(2) | 0.9440(11) | 110(6) | 98(4) | 241(7) | −36(3) | 30(5) | −77(5) |
| O12 | 0.2653(2) | 0.2862(1) | 1.1070(8) | 124(4) | 82(5) | 169(9) | −25(5) | 23(6) | −38(6) |
| C13 | 0.2894(3) | 0.2520(2) | 0.9406(10) | 104(6) | 102(6) | 160(8) | −3(5) | −26(6) | −53(6) |
| C14 | 0.3190(3) | 0.2049(2) | 1.0281(10) | 117(6) | 74(5) | 107(6) | −18(4) | −17(5) | −15(5) |
| C15 | 0.3253(3) | 0.1676(1) | 0.8388(8) | 86(5) | 100(4) | 98(5) | −26(3) | −13(4) | −19(4) |
| N16 | 0.2738(2) | 0.1273(1) | 0.8901(7) | 64(4) | 129(6) | 66(5) | −13(5) | −5(5) | 10(5) |
| C17 | 0.0762(3) | 0.0176(2) | 1.3416(8) | 102(6) | 58(4) | 113(6) | 13(4) | −11(5) | −9(5) |
| C18 | 0.1109(2) | −0.0244(1) | 0.9909(8) | 82(5) | 139(7) | 187(9) | 1(5) | 54(6) | 29(7) |
| C19 | −0.1098(3) | 0.0529(2) | 1.2197(10) | 79(5) | 116(6) | 123(8) | 10(6) | −19(6) | 22(6) |
| C20 | −0.0528(3) | 0.1729(2) | 0.6272(9) | 149(7) | 86(6) | 338(15) | −8(6) | 0(11) | 21(9) |
| C21 | 0.1829(4) | 0.3056(2) | 0.7748(15) | 175(9) | 80(5) | 108(6) | −29(4) | −5(5) | −6(5) |
| C22 | 0.4128(3) | 0.1527(2) | 0.7991(8) | 80(5) | 261(11) | 237(13) | 28(8) | 54(9) | 146(11) |
| C23 | 0.4521(4) | 0.1784(3) | 0.6109(13) | 141(8) | 111(6) | 111(7) | −5(5) | 3(5) | 21(6) |
| C24 | 0.4477(3) | 0.1216(2) | 0.9319(9) | 88(5) | 96(5) | 119(7) | −12(4) | 2(5) | −2(6) |
| C25 | 0.5303(3) | 0.1032(2) | 0.9346(9) | 76(5) | 192(7) | 114(6) | 2(5) | −6(5) | 3(6) |
| N26 | 0.5822(2) | 0.1091(2) | 0.7577(8) | 71(5) | 165(7) | 125(7) | −5(6) | −13(6) | −19(7) |
| C27 | 0.6498(3) | 0.0890(2) | 0.7986(10) | 98(6) | 128(2) | 173(2) | 12(1) | −25(2) | 0(2) |
| S28 | 0.6565(1) | 0.0612(1) | 1.0487(3) | 107(1) | 122(6) | 166(9) | 4(5) | 3(6) | 43(7) |
| C29 | 0.5605(3) | 0.0785(2) | 1.1053(10) | 93(6) | 443(17) | 150(10) | 45(10) | 18(7) | −17(12) |
| C30 | 0.7206(4) | 0.0891(3) | 0.6410(12) | 102(7) | | | | | |

TABLE 7

Hydrogen Positions: Form B

| Atom | X | Y | Z | U*10E2 |
|---|---|---|---|---|
| H21 | 0.1283(0) | 0.0616(0) | 0.7084(0) | 4.86(0) |
| H22 | 0.2159(0) | 0.0306(0) | 0.7857(0) | 4.86(0) |
| H31 | 0.1272(0) | 0.0969(0) | 1.0910(0) | 4.51(0) |
| H3 | 0.2243(0) | 0.0785(0) | 1.3075(0) | 6.11(0) |
| H61 | −0.0043(0) | 0.0983(0) | 1.2199(0) | 4.99(0) |
| H71 | −0.1059(0) | 0.0964(0) | 0.8057(0) | 5.69(0) |
| H7 | −0.1609(0) | 0.1655(0) | 0.9542(0) | 7.62(0) |
| H81 | 0.0313(0) | 0.1244(0) | 0.7484(0) | 5.58(0) |
| H91 | −0.0180(0) | 0.2062(0) | 1.0453(0) | 6.10(0) |
| H92 | 0.0520(0) | 0.1619(0) | 1.1189(0) | 6.10(0) |
| H101 | 0.1365(0) | 0.1874(0) | 0.7953(0) | 7.47(0) |
| H102 | 0.0691(0) | 0.2349(0) | 0.7527(0) | 7.47(0) |
| H111 | 0.0976(0) | 0.2651(0) | 1.1204(0) | 7.74(0) |
| H112 | 0.1633(0) | 0.2170(0) | 1.1686(0) | 7.74(0) |
| H131 | 0.3308(0) | 0.2613(0) | 0.8107(0) | 7.31(0) |
| H141 | 0.3779(0) | 0.2094(0) | 1.1016(0) | 7.61(0) |
| H142 | 0.2780(0) | 0.1920(0) | 1.1530(0) | 7.61(0) |
| H151 | 0.3046(0) | 0.1836(0) | 0.6859(0) | 5.74(0) |
| H16 | 0.2693(0) | 0.1161(0) | 1.0487(0) | 5.71(0) |
| H171 | 0.0304(0) | −0.0088(0) | 1.3753(0) | 6.33(0) |
| H172 | 0.1318(0) | 0.0064(0) | 1.4171(0) | 6.33(0) |
| H173 | 0.0577(0) | 0.0512(0) | 1.4165(0) | 6.33(0) |
| H181 | 0.0633(0) | −0.0501(0) | 1.0184(0) | 5.58(0) |
| H182 | 0.1192(0) | −0.0207(0) | 0.8122(0) | 5.58(0) |
| H183 | 0.1655(0) | −0.0370(0) | 1.0628(0) | 5.58(0) |
| H191 | −0.1481(0) | 0.0774(0) | 1.3099(0) | 8.04(0) |
| H192 | −0.1459(0) | 0.0330(0) | 1.1036(0) | 8.04(0) |
| H193 | −0.0849(0) | 0.0274(0) | 1.3402(0) | 8.04(0) |
| H201 | −0.0094(0) | 0.1955(0) | 0.5429(0) | 7.89(0) |
| H202 | −0.0763(0) | 0.1475(0) | 0.5059(0) | 7.89(0) |
| H203 | −0.1024(0) | 0.1951(0) | 0.6816(0) | 7.89(0) |
| H211 | 0.1596(0) | 0.2886(0) | 0.6259(0) | 11.47(0) |
| H212 | 0.1382(0) | 0.3292(0) | 0.8404(0) | 11.47(0) |
| H213 | 0.2355(0) | 0.3265(0) | 0.7267(0) | 11.47(0) |
| H231 | 0.5051(0) | 0.1602(0) | 1.0559(0) | 6.57(0) |
| H291 | 0.5291(0) | 0.0702(0) | 1.2584(0) | 7.73(0) |
| H301 | 0.7003(0) | 0.0920(0) | 0.4744(0) | 13.05(0) |
| H302 | 0.7623(0) | 0.1165(0) | 0.6811(0) | 13.05(0) |
| H303 | 0.7525(0) | 0.0542(0) | 0.6572(0) | 13.05(0) |

Based on the foregoing data, it is concluded that Forms A and B are unique crystalline entities.

The following non-limiting examples serve to illustrate the practice of the invention.

EXAMPLE 1

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione.

To a jacketed 125 mL round bottom flask, fitted with a mechanical stirrer, there was combined epothilone-B (5.08 g), tetrabutylammonium azide ($Bu_4NN_3$) (3.55 g, 1.25 equivalents), ammonium chloride (1.07 g, 2 eq), water (1.8 ml, 10 equivalents), tetrahydrofuran (THF) (15 ml), and N,N-dimethylformamide (DMF) (15 ml). The mixture was inerted by sparging nitrogen subsurface for 15 minutes. In a second flask was charged tetrahydrofuran (70 ml), followed by trimethylphosphine ($PMe_3$) (1.56 ml, 1.5 equivalents), then tris(dibenzilideneacetone)-dipalladium(0)-chloroform adduct ($Pd_2(dba)_3CHCl_3$)(0.259 g, 0.025 equivalents). The catalyst mixture was stirred for 20 minutes at ambient temperature, then added to the epothilone-B mixture. The combined mixture was stirred for 4.5 hours at 30° C. The completed reaction mixture was then filtered to remove solid ammonium chloride ($NH_4Cl$). The filtrate contained (βS, εR, ζS, ηS, 2R, 3S)-3-[(2S, 3E)-2-amino-3-methyl-4-(2-methyl-4-thiazolyl)-3-butenyl]-β, ζ-dihydroxy-γ, γ, ε, η, 2-pentamethyl-6-oxooxiraneundecanoic acid, tetrabutylammonium salt (1:1) with a HPLC area of 94.1%.

In a 500 mL flask there was combined 1-[3-(dimethylamino)propyl]-3-ethylcarbodiimide hydrochloride (EDCI) (3.82 g, 2 equivalents), 1-hydroxy-7-benzotriazole hydrate (HOBt) (1.68 g, 1.1 equivalents), potassium carbonate (1.38 g, 1 equivalent), N, N-dimethylformamide (DMF) (40 ml) and tetrahydrofuran (THF) (160 ml). The mixture was warmed to 35° C. and the filtrate from above was added thereto, dropwise over a period of three hours. This mixture was then stirred for an additional 1 hour at 35° C. Vacuum distillation was then applied to the reaction mixture to reduce the volume thereof to about 80 mL. The resulting solution was partitioned between 100 mL of ethyl acetate and 100 mL of water. The aqueous layer was then back-extracted with 100 ml ethyl acetate. The combined organic layers were extracted with 50 ml water and then 20 mL brine. The resulting product solution was filtered through a Zeta Plus® pad and then stripped to an oil. The crude oil was dissolved in dichloromethane (20 mL) and washed with water to remove final traces of synthesis solvents and stripped to a solid. The crude solid was chromatographed on silica gel 60 (35 ml silica per gram of theoretical product) with an eluent comprised of 88% dichloromethane ($CH_2Cl_2$), 10%–30% ethyl acetate (EtOAc) and 2% triethylamine ($Et_3N$). The fractions were analyzed by HPLC, the purest of which were combined and stripped to give the purified solid. The resulting solid, approx. 2 g, was slurried in ethyl acetate (32 ml) for 40 minutes at 75° C., then cyclohexane ($C_6H_{12}$) (16 ml) was slowly added, and the mixture cooled to 5° C. The purified solid was collected on filter paper, washed with cold ethyl acetate/cyclohexane, and dried. The yield was 1.72 g (38% yield) of the white solid product, [1S-[1R*,3R*(E),7R*, 10S*, 11R*, 12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, with a HPLC area of 99.2%.

EXAMPLE 2

[1S-[1R*,3R*(E),7R*,10S*, 11R*,12R*, 16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, Form A.

A 250 mL three-neck flask was charged with 0.61 g of the title compound that had been purified (silica gel pad filtration with EtOAc/hexane/$Et_3N$ as the eluent, HPLC area of 96.88) and ethyl acetate (28 mL, 46 ml/1 g). The resultant slurry was heated to 75° C. All of solids were dissolved after the slurry was stirred at 75° C. for 60 minutes. The afforded solution was cooled from 75° C. to 50° C. over 120 minutes, seed crystals of Form A being added at 60° C. Crystals appeared at 55° C. The temperature was thereafter cooled to 20° C. over 120 minutes, while cyclohexane (35 mL, 57 mL/1 g) was added dropwise to the mixture over a period of 60 minutes. The obtained slurry was cooled to −10° C. over 120 minutes, and maintained for an additional 60 minutes. The slurry was filtered and the afforded white crystals were dried to give 0.514 g of the title compound, Form A, in 84.3% yield with an HPLC area of 99.4.

Form A—Alternate Procedure

A 250 mL three-neck flask was charged with 0.51 g of the title compound that had been purified (silica gel pad filtration with EtOAc/hexane/$Et_3N$ as the eluent, HPLC area of 96) and ethyl acetate (8.5 mL, 16.7 ml/1 g). The resultant slurry was heated to 80° C. The afforded solution was cooled from 80° C. to 70° C. over 60 minutes, seed crystals of Form A being added at 70° C. The temperature was thereafter cooled to 30° C. over 180 minutes. Crystals appeared at 65° C. The solution was further cooled to −10° C. over 180 minutes, while cyclohexane (10.2 mL, 20 mL/1 g) was added dropwise to the mixture over a period of 30 minutes. The obtained slurry was cooled maintained for an additional 60 minutes. The slurry was filtered and the afforded white crystals were dried to give 0.43 g of the title compound, Form A, in 84.3% yield with an HPLC area of 99.7.

Form A—Alternate Procedure

A 500 mL three-neck flask was charged with 18.3 g of a mixture of Forms A and B that had been purified (silica gel pad filtration with EtOAc/dichloromethane/$Et_3N$ as the eluent, HPLC area of 99) and ethyl acetate (183 mL, 10 ml/1 g). The resultant slurry was heated to 75° C., seed crystals of Form A were added and the temperature was maintained for 30 minutes. Cyclohexane (90.2 mL, 5 mL/1 g) was added dropwise to the mixture keeping the temperature at 70° C. After completion of the addition, the temperature was lowered to 20° C. and the mixture maintained with stirring for a further 18 hours. The temperature was thereafter lowered to 5° C. and maintain for 5 hours. The slurry was filtered and the afforded white crystals were dried to give 16.1 g of the title compound, Form A, in 88% yield with an HPLC area of 99.49.

EXAMPLE 3

[1S-[1R*,3R*(E),7R*, 10S*, 1R*,12R*, 16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione, Form B.

A 250 mL three-neck flask was charged with 0.108 g of the title compound that had not been purified as in Example 2, N,N-dimethyl formamide (0.0216 g) and ethyl acetate (5 mL, 46 ml/1 g). The resultant slurry was heated to 80° C. and stirred for 30 minutes to dissolve all solids. The afforded solution was cooled from 80° C. to 30° C. over 120 minutes, crystals appearing at 38° C. Cyclohexane (7.5 mL, 69.5 mL/1 g) was added dropwise to the mixture over a period of 30 minutes while the temperature was cooled to −10° C. over 60 minutes, and maintained for an additional 120 minutes. The slurry was filtered and the afforded white crystals were dried to give 0.082 g of the title compound, Form B, in 76% yield with an HPLC area of 99.6.

Form—Alternate Procedure

A 250 mL three-neck flask was charged with 0.458 g of the title compound that had not been purified as in Example 2 and contained about 6% of N,N-dimethyl formamide and ethyl acetate (10 mL, 21.8 ml/1 g). The resultant slurry was heated to 78° C. and stirred for 30 minutes to dissolve all solids. The afforded solution was cooled from 78° C. to 10° C. over 120 minutes. Seed crystals of Form A were added at 10° C. Cyclohexane (20 mL, 43.7 mL/1 g) was added dropwise to the mixture over a period of 60 minutes while the temperature was cooled to −10° C. over 120 minutes, and maintained for an additional 120 minutes. The slurry was filtered and the afforded white crystals were dried to give 0.315 g of the title compound, Form B, in 68.8% yield with an HPLC area of 98.2.

Form B—Alternate Procedure

A 5-mL Wheaton bottle was charged with 250 mg of the title compound that had not been purified as in Example 2 and toluene (3.75 mL, 15 mL/g.) and the resultant slurry heated to 75° C. and held for 30 minutes. The resultant suspension was allowed to cool to 20° C. and maintained at that temperature for 18 hours with stirring. The slurry was filtered and the afforded white crystals dried to give 150 mg. of the title compound, Form B, in 60% yield with an HPLC area of 99.2

We claim:

1. A crystalline polymorph of an epothilone analog represented by the formula

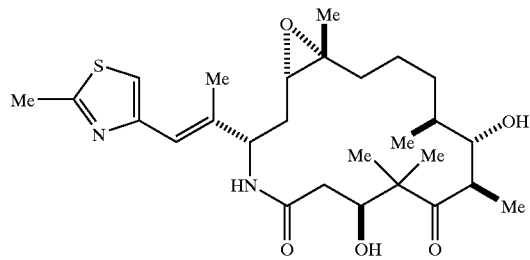

I comprising Form A characterized by:

unit cell parameters approximately equal to the following:

| Cell dimensions | a = 14.152(6) Å |
| --- | --- |
| | b = 30.72(2) Å |
| | c = 6.212(3) Å |
| | Volume = 2701(4) A$^3$ |
| Space group | P2$_1$2$_1$2$_1$ |
| | Orthorhombic |
| Molecules/unit cell | 4 |
| Density (calculated) (g/cm$^3$) | 1.247 |
| Melting point | 182–185° C. (decomposition); and | characteristic peaks in the powder x-ray diffraction pattern at values of two theta (CuKα λ=1.5406 Å at 22° C.): 5.69, 6.76, 8.38, 11.43, 12.74, 13.62, 14.35, 15.09, 15.66, 16.43, 17.16, 17.66, 18.31, 19.03, 19.54, 20.57, 21.06, 21.29, 22.31, 23.02, 23.66, 24.18, 14.98, 25.50, 26.23, 26.23, 26.46, 27.59, 28.89, 29.58, 30.32, 31.08 and 31.52.

2. A crystalline polymorph of an epothilone analog represented by the formula

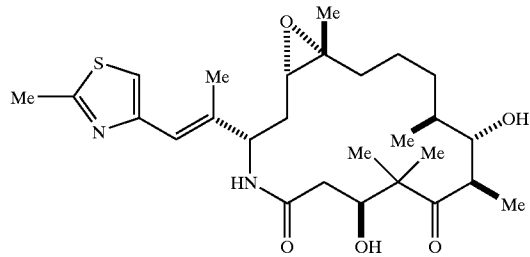

I comprising Form A characterized by powder x-ray diffraction substantially as shown in FIG. 1 and a Raman spectrum substantially as shown in FIG. 5.

3. A crystalline polymorph of an epothilone analog represented by the formula

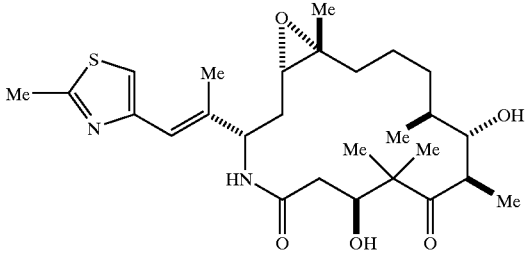

I comprising Form A characterized by a solubility in water of 0.1254, a solubility in a 3% aqueous solution of polysorbate 80 of 0.2511, a melting point with decomposition between 182–185° C. and a heat of solution of 20.6 kJ/mol.

4. A crystalline material of an epothilone analog represented by formula I:

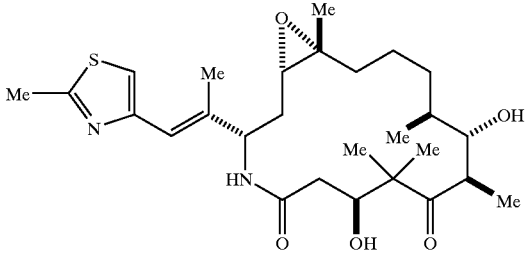

I comprising a mixture of Form A and Form B wherein Form A is characterized by:

unit cell parameters approximately equal to the following:

| Cell dimensions | a = 14.152(6) Å |
| --- | --- |
| | b = 30.72(2) Å |
| | c = 6.212(3) Å |
| | Volume = 2701(4) A$^3$ |
| Space group | P2$_1$2$_1$2$_1$ |
| | Orthorhombic |
| Molecules/unit cell | 4 |
| Density (calculated) (g/cm$^3$) | 1.247 |
| Melting point | 182–185° C. (decomposition); and | characteristic peaks in the powder x-ray diffraction pattern at values of two theta (CuKα λ=1.5406 Å at 22° C.): 5.69, 6.76, 8.38, 11.43, 12.74, 13.62, 14.35, 15.09, 15.66, 16.43, 17.16, 17.66, 18.31, 19.03, 19.54, 20.57, 21.06, 21.29, 22.31, 23.02, 23.66, 24.18, 14.98, 25.50, 26.23, 26.23, 26.46, 27.59, 28.89, 29.58, 30.32, 31.08 and 31.52;

and Form B is characterized by:

unit cell parameters approximately equal to the following:

| Cell dimensions | a = 16.675(2) Å |
| --- | --- |
| | b = 28.083(4) Å |
| | c = 6.054(1) Å |
| | Volume = 2835(1) A$^3$ |
| Space group | P2$_1$2$_1$2$_1$ |
| | Orthorhombic |

| | |
|---|---|
| Molecules/unit cell | 4 |
| Density (calculated) (g/cm³) | 1.187 |
| Melting point | 191–199° C. decomposition; and | characteristic peaks in the powder x-ray diffraction pattern at values of two theta (CuKα λ=1.5406 Å at 22° C.): 6.17, 10.72, 12.33, 14.17, 14.93, 15.88, 16.17, 17.11, 17.98, 19.01, 19.61, 20.38, 21.55, 21.73, 22.48, 23.24, 23.93, 24.78, 25.15, 25.90, 26.63, 27.59, 28.66, 29.55, 30.49 and 31.22.

5. A crystalline material of an epothilone analog represented by formula I;

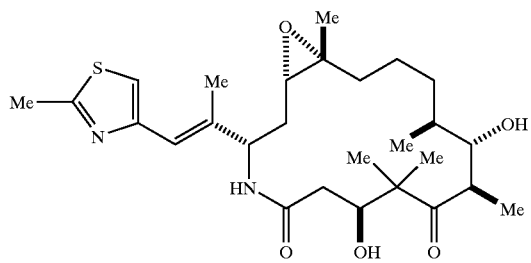

comprising a mixture of Form A and Form B wherein Form A is characterized by powder x-ray diffraction substantially as shown in FIG. 1 and a Raman spectrum substantially as shown in FIG. 5;
and Form B is characterized by powder x-ray diffraction substantially as shown in FIG. 2 and a Raman spectrum substantially as shown in FIG. 6.

6. A crystalline material of an epothilone analog represented by formula I:

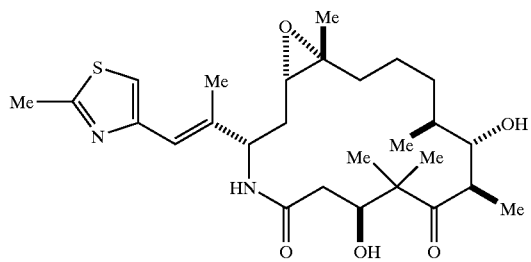

comprising a mixture of Form A and Form B wherein Form A is characterized by a solubility in water of 0.1254, a solubility in a 3% aqueous solution of polysorbate 80 of 0.2511, a melting point with decomposition between 182–185° C. and a heat of solution of 20.6 kJ/mol;
and Form B is characterized by a solubility in water of 0.1907, a solubility in a 3% aqueous solution of polysorbate 80 of 0.5799, a melting point with decomposition between 191–199° C. and a heat of solution of 9.86 kJ/mol.

7. A process for producing a crystalline polymorph that is Form A of the epothilone analog represented by formula I in claim 1 comprising heating a slurry of said analog represented by formula I in from about 8 to about 16 mL of ethyl acetate per gram of said analog to about 75° C. maintaining the temperature for about one hour, adding an amount of cyclohexane in a ratio to the amount of ethyl acetate of from about 1:2 to about 2:2, allowing the mixture to cool to ambient temperature, maintain the mixture with stirring from about 12 to 96 hours, further cooling it to about 5° C. over about two hours and recovering the crystalline Form A therefrom.

8. A process in accordance with claim 7 wherein the amount of cyclohexane added is in a 1:2 ratio to the amount of ethyl acetate utilized to form said slurry.

9. A process in accordance with claim 7 wherein said slurry of said analog represented by formula I in ethyl acetate is heated to about 75° C. seed crystals are added thereto and the mixture is maintained for about 30 minutes after which said amount of cyclohexane is added thereto while maintaining the mixture at about 70° C., cooling the mixture to ambient temperature, maintain the mixture with stirring for about 18 hours, further cooling it to about 5° C. over about two hours and recovering the crystalline Form A therefrom.

10. A process in accordance with claim 7 wherein said slurry of said analog represented by formula I in ethyl acetate is heated to about 75° C. for at least an hour until a solution is formed, cooling said solution to about 50° C. over about two hours, adding said seed crystals thereto when the temperature reaches about 60° C., cooling the solution to about 30° C. over about three hours, further reducing the temperature of the solution to −10° C. over about three hours during one hour of which said amount of cyclohexane is added thereto dropwise, maintaining the resultant mixture at −10° C. for about one hour and recovering the crystalline Form A therefrom.

11. A process for producing a crystalline polymorph that is Form B of the epothilone analog represented by formula I in claim 8 comprising heating a slurry of said analog represented by formula I in from about 40 to about 50 mL of ethyl acetate per gram of said analog to about 75° C. to 80° C., maintaining the temperature for about one hour thereby forming a solution, maintaining the solution at temperature for about 30 minutes, cooling the solution to about 30° C. over about two hours, further reducing the temperature of the solution to −10° C. over about one hour during which an amount of cyclohexane in a ratio to the amount of ethyl acetate of from about 1:2 to about 2:2 is added thereto dropwise over a period of about thirty minutes, maintaining the resultant mixture at −10° C. for about two hours and recovering the crystalline Form B therefrom.

12. A process in accordance with claim 11 wherein said slurry of said analog represented by formula I in ethyl acetate is heated to about 78° C. thereby forming a solution, cooling the solution to about 10° C. over about two hours, adding seed crystals when the temperature reaches 10° C., further reducing the temperature of the solution to −10° C. over about two hours during which said amount of cyclohexane is added thereto dropwise over a period of about thirty minutes, maintaining the resultant mixture at −10° C. for about two hours and recovering the crystalline Form B therefrom.

13. A crystalline polymorph of an epothilone analog represented by the formula

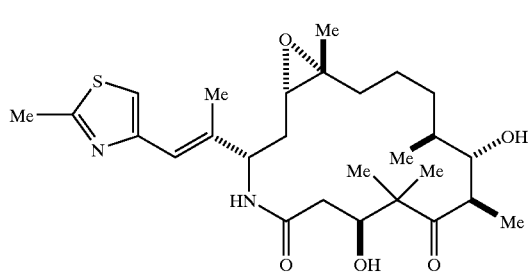

comprising Form B characterized by:

unit cell parameters approximately equal to the following:

| Cell dimensions | a = 16.675(2) Å |
| --- | --- |
|  | b = 28.083(4) Å |
|  | c = 6.054(1) Å |
|  | Volume = 2835(1) A$^3$ |
| Space group | P2$_1$2$_1$2$_1$ |
|  | Orthorhombic |
| Molecules/unit cell | 4 |
| Density (calculated) (g/cm$^3$) | 1.187 |
| Melting point | 191–199° C. decomposition; and | characteristic peaks in the powder x-ray diffraction pattern at values of two theta (CuKα λ=1.5406 Å at 22° C.): 6.17, 10.72, 12.33, 14.17, 14.93, 15.88, 16.17, 17.11, 17.98, 19.01, 19.61, 20.38, 21.55, 21.73, 22.48, 23.24, 23.93, 24.78, 25.15, 25.90, 26.63, 27.59, 28.66, 29.55, 30.49 and 31.22.

14. A process for producing a crystalline polymorph that is Form B of the epothilone analog represented by formula I in claim 13 comprising heating a slurry of said analog represented by formula I in from about 10 to about 20 mL of toluene per gram of said analog to about 75° C. to 80° C., maintaining the temperature for about 30 minutes, cooling the mixture to about 20° C., maintaining the temperature for about 18 hours with stirring and recovering the crystalline Form B therefrom.

15. A pharmaceutical composition which comprises as an active ingredient an effective amount a crystalline polymorph as claimed in claim 1 and one or more pharmaceutically acceptable carriers, excipients or diluents thereof.

16. A pharmaceutical composition which comprises as an active ingredient an effective amount a crystalline polymorph as claimed in claim 2 and one or more pharmaceutically acceptable carriers, excipients or diluents thereof.

17. A pharmaceutical composition which comprises as an active ingredient an effective amount a crystalline polymorph as claimed in claim 3 and one or more pharmaceutically acceptable carriers, excipients or diluents thereof.

18. A pharmaceutical composition which comprises as an active ingredient an effective amount of a crystalline polymorph of an epothilone analog represented by formula I:

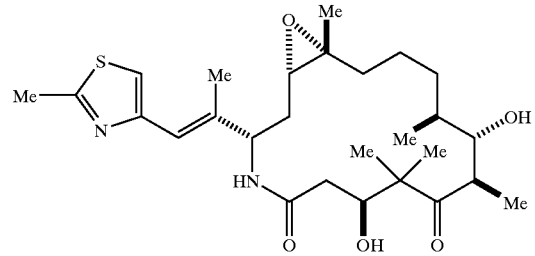

and one or more pharmaceutically acceptable carriers, wherein said crystalline polymorph is a mixture of Form A and Form B, wherein Form A is characterized by:

unit cell parameters approximately equal to the following:

| Cell dimensions | a = 14.152(6) Å |
| --- | --- |
|  | b = 30.72(2) Å |
|  | c = 6.212(3) Å |
|  | Volume = 2701(4) A$^3$ |
| Space group | P2$_1$2$_1$2$_1$ |
|  | Orthorhombic |
| Molecules/unit cell | 4 |
| Density (calculated) (g/cm$^3$) | 1.247 |
| Melting point | 182–185° C. (decomposition); and | characteristic peaks in the powder x-ray diffraction pattern at values of two theta (CuKα λ=1.5406 Å at 22° C.): 5.69, 6.76, 8.38, 11.43, 12.74, 13.62, 14.35, 15.09, 15.66, 16.43, 17.16, 17.66, 18.31, 19.03, 19.54, 20.57, 21.06, 21.29, 22.31, 23.02, 23.66, 24.18, 14.98, 25.50, 26.23, 26.23, 26.46, 27.59, 28.89, 29.58, 30.32, 31.08 and 31.52;

and Form B is characterized by:

unit cell parameters approximately equal to the following:

| Cell dimensions | a = 16.675(2) Å |
| --- | --- |
|  | b = 28.083(4) Å |
|  | c = 6.054(1) Å |
|  | Volume = 2835(1) A$^3$ |
| Space group | P2$_1$2$_1$2$_1$ |
|  | Orthorhombic |
| Molecules/unit cell | 4 |
| Density (calculated) (g/cm$^3$) | 1.187 |
| Melting point | 191–199° C. decomposition; and | characteristic peaks in the powder x-ray diffraction pattern at values of two theta (CuKα λ=1.5406 Å at 22° C.): 6.17, 10.72, 12.33, 14.17, 14.93, 15.88, 16.17, 17.11, 17.98, 19.01, 19.61, 20.38, 21.55, 21.73, 22.48, 23.24, 23.93, 24.78, 25.15, 25.90, 26.63, 27.59, 28.66, 29.55, 30.49 and 31.22.

19. A method for treating cancer or other proliferative diseases which comprises administering to a mammal in need thereof an effective amount of a crystalline polymorph as claimed in claim 1.

20. A method for treating cancer or other proliferative diseases which comprises administering to a mammal in need thereof an effective amount of a crystalline polymorph as claimed in claim 2.

21. A method for treating cancer or other proliferative diseases which comprises administering to a mammal in need thereof an effective amount of a crystalline polymorph as claimed in claim 3.

22. A method in accordance with claim 19 wherein said crystalline polymorph is administered parenterally.

23. A crystalline polymorph of an epothilone analog represented by the formula

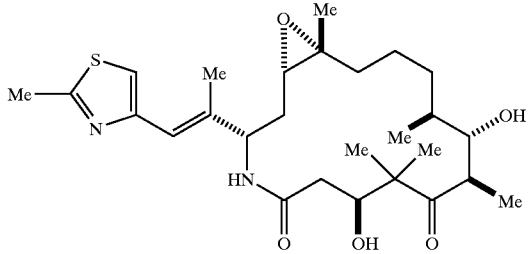

I comprising Form B characterized by powder x-ray diffraction substantially as shown in FIG. 2 and a Raman spectrum substantially as shown in FIG. 6.

24. A crystalline polymorph of an epothilone analog represented by the formula

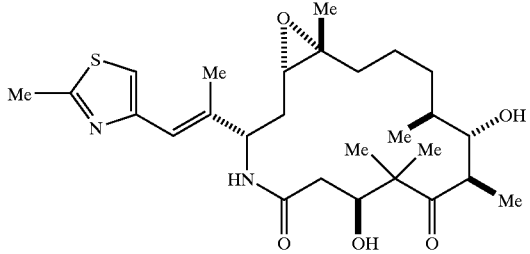

I comprising Form B characterized by a solubility in water of 0.1907, a solubility in a 3% aqueous solution of polysorbate 80 of 0.5799, a melting point with decomposition between 191–199° C. and a heat of solution of 9.86 kJ/mol.

25. A pharmaceutical composition which comprises as an active ingredient an effective amount a crystalline polymorph as claimed in claim 13 and one or more pharmaceutically acceptable carriers, excipients or diluents thereof.

26. A pharmaceutical composition which comprises as an active ingredient an effective amount a crystalline polymorph as claimed in claim 23 and one or more pharmaceutically acceptable carriers, excipients or diluents thereof.

27. A pharmaceutical composition which comprises as an active ingredient an effective amount a crystalline polymorph as claimed in claim 24 and one or more pharmaceutically acceptable carriers, excipients or diluents thereof.

28. A method for treating cancer or other proliferative diseases which comprises administering to a mammal in need thereof an effective amount of a crystalline polymorph as claimed in claim 13.

29. A method for treating cancer or other proliferative diseases which comprises administering to a mammal in need thereof an effective amount of a crystalline polymorph as claimed in claim 23.

30. A method for treating cancer or other proliferative diseases which comprises administering to a mammal in need thereof an effective amount of a crystalline polymorph as claimed in claim 24.

31. A method in accordance with claim 28 wherein said crystalline polymorph is administered parenterally.

* * * * *